(12) United States Patent
Knust et al.

(10) Patent No.: US 8,318,749 B2
(45) Date of Patent: Nov. 27, 2012

(54) QUINAZOLINE DERIVATIVES AS NK3 RECEPTOR ANTAGONISTS

(75) Inventors: Henner Knust, Rheinfelden (DE); Anja Limberg, Basel (CH); Matthias Nettekoven, Grenzach-Wyhien (DE); Hasane Ratni, Habsheim (FR); Claus Riemer, Freiburg (DE); Walter Vifian, Gelterkinden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 293 days.

(21) Appl. No.: 12/614,474

(22) Filed: Nov. 9, 2009

(65) Prior Publication Data

US 2010/0125078 A1    May 20, 2010

(30) Foreign Application Priority Data

Nov. 14, 2008    (EP) ..................... 08169162

(51) Int. Cl.
A61K 31/517    (2006.01)
C07D 239/70    (2006.01)
C07D 401/04    (2006.01)

(52) U.S. Cl. .................. 514/258.1; 544/242; 544/253; 544/283; 514/256

(58) Field of Classification Search .................. 544/242, 544/253, 283; 514/256, 258.1
See application file for complete search history.

(56) References Cited

U.S. PATENT DOCUMENTS

| 4,243,666 | A | 1/1981 | Campbell et al. | |
| 7,678,802 | B2 * | 3/2010 | Gonzalez et al. | 514/266.2 |
| 7,713,983 | B2 * | 5/2010 | Gonzalez et al. | 514/266.1 |
| 2004/0248890 | A1 | 12/2004 | Gonzalez, III et al. | |
| 2005/0182093 | A1 | 8/2005 | Farina et al. | |

FOREIGN PATENT DOCUMENTS

| EP | 0034471 | 8/1981 |
| WO | 9532205 | 11/1995 |
| WO | 9723462 | 7/1997 |
| WO | 2004078733 | 9/2004 |

OTHER PUBLICATIONS

Alabaster et al (1987): STN International HCAPLUS database, (Columbus, Ohio), Accession No. 1987:407164.*
Tooney et al , Neurosci. Letters, 2000, vol. 283, pp. 185-188.
Giardina et al., Exp. Opin. Ther. Patents, 2000, vol. 10, pp. 939-960.
Jung et al., Neurosci., 1996, vol. 74, pp. 403-414.
Marco et al., Neuropeptides, 1998, vol, 32, pp. 481-488.
Kamali, F., Current Opinion in Investigational Drugs, 2001 vol. 2(7), pp. 950-956.
Zeghida et al. J. Org. Chem 2008 vol. 73 p. 2473-2475.

* cited by examiner

*Primary Examiner* — Golam M M Shameem
(74) *Attorney, Agent, or Firm* — George W. Johnston; Patricia S. Rocha-Tramaloni; Kimberly J. Prior

(57) ABSTRACT

The present invention relates to a compounds of formula I

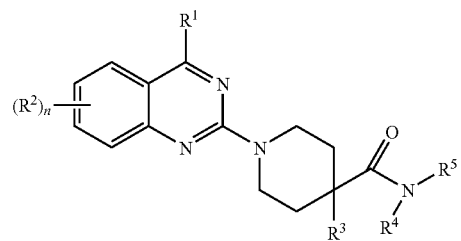

wherein
$R^1$, $R^2$, $R^3$, $R^4$, $R^5$, and n are as defined herein and to a pharmaceutically active salt, a racemic mixture, an enantiomer, an optical isomer or a tautomeric form thereof. The present compounds are high potential NK-3 receptor antagonists for the treatment of depression, pain, psychosis, Parkinson's disease, schizophrenia, anxiety and attention deficit hyperactivity disorder (ADHD).

19 Claims, No Drawings

QUINAZOLINE DERIVATIVES AS NK3 RECEPTOR ANTAGONISTS

PRIORITY TO RELATED APPLICATION(S)

This application claims the benefit of European Patent Application No. 08169162.8, filed Nov. 14, 2008, which is hereby incorporated by reference in its entirety.

BACKGROUND OF THE INVENTION

The three main mammalian tachykinins, substance P(SP), neurokinin A (NKA) and neurokinin B (NKB) belong to the family of neuropeptides sharing the common COOH-terminal pentapeptide sequence of Phe-X-Gly-Leu-Met-NH$_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001, 2(7), 950-956 and *Psychiatric Disorders Study* 4, *Schizophrenia, June* 2003, Decision Recources, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, Schizophrenia, June 2003, Decision Recources, Inc., Waltham, Mass.).

SUMMARY OF THE INVENTION

The present invention provides novel compounds of formula I, their manufacture, pharmaceutical compositions containing them and methods for treating illnesses such as depression, pain, bipolar disorders, psychosis, Parkinson's disease, schizophrenia, anxiety and attention deficit hyperactivity disorder (ADHD) with them.

The present invention provides compounds of formula I

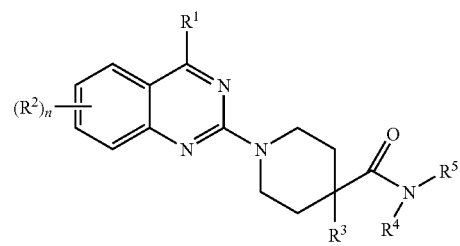

wherein
$R^1$ is hydroxy or NR'R";
   R' and R" are each independently hydrogen, lower alkyl, cycloalkyl, or together with the N-atom to which they are attached form a heteroalkyl ring;
$R^2$ is hydrogen, lower alkyl, lower alkoxy, halogen, lower alkyl substituted by halogen, lower alkoxy substituted by halogen, cyano or S(O)$_2$-lower alkyl;
$R^3$ is lower alkyl, —(CH$_2$)$_m$-aryl optionally substituted by halogen, or —(CH$_2$)$_m$-cycloalkyl;
$R^4$ and $R^5$ are each independently
   hydrogen,
   lower alkyl substituted by halogen,
   —(CR$_2$)$_m$-aryl or —(CR$_2$)$_m$-heteroaryl, wherein the aryl and heteroaryl is optionally substituted by one or more substituents selected from halogen, lower alkyl, lower alkyl substituted by halogen, cyano, hydroxy, NR'R" or by lower alkoxy substituted by halogen,
   —(CR$_2$)$_m$-cycloalkyl optionally substituted by hydroxy or by aryl,
   a heteroalkyl ring, optionally substituted by =O or —(CR$_2$)$_m$-aryl, or $R^4$ and $R^5$ together with the N-atom to which they are attached form a heterocyclic ring system, optionally substituted by lower alkyl, aryl or halogen-substituted aryl, and each R is independently hydrogen, lower alkyl or lower alkyl substituted by hydroxyl;

n is 1 or 2; and m is 0, 1 or 2;

or to a pharmaceutically active salt, a racemic mixture, an enantiomer, an optical isomer or a tautomeric form thereof.

The invention includes all stereoisomeric forms, including individual diastereoisomers and enantiomers of the compound of formula (I) as well as racemic and non-racemic mixtures thereof.

The present compounds are high potential NK-3 receptor antagonists for the treatment of depression, pain, psychosis, Parkinson's disease, schizophrenia, anxiety and attention deficit hyperactivity disorder (ADHD).

The preferred indications are depression, psychosis, Parkinson's disease, schizophrenia, anxiety and attention deficit hyperactivity disorder (ADHD).

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes a lower alkyl group as defined above, wherein at least one hydrogen atom is replaced by halogen, for example —$CF_3$, —$CHF_2$, —$CH_2F$, —$CH_2CF_3$, —$CH_2CH_2CF_3$, —$CH_2CF_2CF_3$ and the like. Preferred lower alkyl substituted by halogen groups are groups having 1-4 carbon atoms.

The term "lower alkoxy" denotes a group —O—R' wherein R' denotes a lower alkyl group as defined above. Examples for "alkoxy" are methoxy, ethoxy, propoxy, tert-butoxy and the like. Preferred are methoxy and tert-butoxy.

The term "lower alkoxy substituted by halogen" denotes a lower alkoxy group as defined above wherein at least one hydrogen atom is replaced by halogen, for example —$OCF_3$, —$OCHF_2$, —$OCH_2F$, —$OCH_2CF_3$, —$OCH_2CH_2CF_3$, —$OCH_2CF_2CF_3$ and the like.

The term "halogen" denotes chlorine, iodine, fluorine and bromine.

The term "cycloalkyl" denotes a saturated carbon ring containing from 3-7 carbon atoms, for example, cyclopropyl, cyclobutyl, cyclopentyl, cyclohexyl, cycloheptyl, and the like.

The term "aryl" denotes a cyclic aromatic hydrocarbon radical consisting of one or more fused rings containing 6-14 carbon atoms in which at least one ring is aromatic in nature, for example phenyl, naphthyl, 1,2,3,4-tetrahydronaphthalenyl or indanyl. Preferred is the phenyl group.

The term "heteroaryl" denotes a cyclic aromatic radical consisting of one or more fused rings containing 5-14 ring atoms, preferably containing 5-10 ring atoms, in which at least one ring is aromatic in nature, and which contains at least one heteroatom, selected from N, O and S, for example quinoxalinyl, dihydroisoquinolinyl, pyrazin-2-yl, pyrazolyl, 2,4-dihydro-pyrazol-3-one, pyridinyl, isoxazolyl, benzo[1,3]dioxol, pyridyl, pyrimidin-4-yl, pyrimidin-5-yl, benzotriazol-5-yl, benzoimidazol-5-yl, [1,3,4]-oxadiazol-2-yl, [1,2,4] triazol-1-yl, [1,6]naphthyridin-2-yl, imidazo[4,5-b]pyridine-6-yl, tetrazolyl, thiazolyl, thiadiazolyl, thienyl, furyl, imidazol-1-yl, or benzofuranyl. Preferred heteroaryl group is pyridine-2,3 or 4-yl.

The term "heteroalkyl" ring denotes a five or six membered saturated ring, containing one or two heteroatoms selected from N, S and O, for example the following groups: morpholinyl, [1,4]diazepam-1-yl, piperazinyl, pyrrolidinyl, piperidin-1-yl, tetrahydrofuranyl, tetrahydrothiophenyl, piperidin-4-yl or 1,1-dioxo-$\lambda^6$-thiomorpholinyl.

The term heterocyclic ring system denotes a group containing one or two ring members, and contains at least one N-atom in 1 position, for example 3,4-dihydro-1H-isoquinolin-1-yl or pyrrolidin-1-yl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of formula I are those, wherein $R^3$ is —$(CH_2)_m$-aryl wherein m is 1 and one of $R^4$ or $R^5$ is —$(CH_2)_m$-heteroaryl optionally substituted by methyl, wherein m is 0 or 1, for example the following compounds 1-(4-amino-6,7-dimethoxy-quinazolin-2-yl)-4-benzyl-piperidine-4-carboxylic acid (pyridin-3-ylmethyl)-amide;

4-benzyl-1-(4-hydroxy-6,7-dimethoxy-quinazolin-2-yl)-piperidine-4-carboxylic acid (pyridin-3-ylmethyl)-amide;

1-(4-amino-6,7-dimethoxy-quinazolin-2-yl)-4-benzyl-piperidine-4-carboxylic acid (furan-2-ylmethyl)-amide; and 4-benzyl-1-(4-hydroxy-6,7-dimethoxy-quinazolin-2-yl)-piperidine-4-carboxylic acid (1-methyl-1H-pyrazol-4-yl)-amide.

Preferred compounds of formula I are further those, wherein $R^3$ is —$(CH_2)_m$-aryl optionally substituted by halogen wherein m is 1 and one of $R^4$ or $R^5$ is —$(CH_2)_m$-phenyl wherein m is 1, for example the following compounds 1-(4-amino-6,7-dimethoxy-quinazolin-2-yl)-4-(4-fluoro-benzyl)-piperidine-4-carboxylic acid benzylamide;

1-(4-amino-6,7-dimethoxy-quinazolin-2-yl)-4-benzyl-piperidine-4-carboxylic acid benzylamide;

4-benzyl-1-(4-dimethylamino-6,7-dimethoxy-quinazolin-2-yl)-piperidine-4-carboxylic acid benzylamide;

4-benzyl-1-(4-cyclopropylamino-6,7-dimethoxy-quinazolin-2-yl)-piperidine-4-carboxylic acid benzylamide;

4-benzyl-1-(7-chloro-6-fluoro-4-hydroxy-quinazolin-2-yl)-piperidine-4-carboxylic acid benzylamide;

4-benzyl-1-(4-hydroxy-6,7-dimethoxy-quinazolin-2-yl)-piperidine-4-carboxylic acid benzylamide;

4-benzyl-1-(4-hydroxy-6,7-dimethoxy-quinazolin-2-yl)-piperidine-4-carboxylic acid benzyl-methyl-amide;

4-benzyl-1-(4-hydroxy-6-isopropoxy-quinazolin-2-yl)-piperidine-4-carboxylic acid benzylamide;

4-benzyl-1-(6-fluoro-4-hydroxy-7-methoxy-quinazolin-2-yl)-piperidine-4-carboxylic acid benzylamide;

4-benzyl-1-(7-difluoromethoxy-4-hydroxy-quinazolin-2-yl)-piperidine-4-carboxylic acid benzylamide;

4-benzyl-1-(4-hydroxy-7-methoxy-6-methyl-quinazolin-2-yl)-piperidine-4-carboxylic acid benzylamide;

4-benzyl-1-(4-hydroxy-6-isopropoxy-7-methoxy-quinazolin-2-yl)-piperidine-4-carboxylic acid benzylamide;

4-benzyl-1-(4-hydroxy-7-isopropoxy-6-methoxy-quinazolin-2-yl)-piperidine-4-carboxylic acid benzylamide;

4-benzyl-1-(6-chloro-4-hydroxy-7-methoxy-quinazolin-2-yl)-piperidine-4-carboxylic acid benzylamide;
4-benzyl-1-(6-difluoromethoxy-7-ethoxy-4-hydroxy-quinazolin-2-yl)-piperidine-4-carboxylic acid benzylamide;
4-benzyl-1-(4-hydroxy-7-methoxy-quinazolin-2-yl)-piperidine-4-carboxylic acid benzylamide;
4-benzyl-1-(4-hydroxy-7-isopropoxy-quinazolin-2-yl)-piperidine-4-carboxylic acid benzylamide;
4-benzyl-1-(6-cyano-4-hydroxy-7-methoxy-quinazolin-2-yl)-piperidine-4-carboxylic acid benzylamide;
4-benzyl-1-(4-hydroxy-7-trifluoromethyl-quinazolin-2-yl)-piperidine-4-carboxylic acid benzylamide; and
4-benzyl-1-(4-hydroxy-7-trifluoromethoxy-quinazolin-2-yl)-piperidine-4-carboxylic acid benzylamide.

Preferred compounds of formula I are further those, wherein $R^3$ is —$(CH_2)_m$-aryl wherein m is 1 and one of $R^4$ or $R^5$ is —$(CH_2)_m$-aryl wherein m is 0 and aryl is other than phenyl optionally substituted by hydroxy or halogen, for example the following compounds
1-(4-amino-6,7-dimethoxy-quinazolin-2-yl)-4-benzyl-piperidine-4-carboxylic acid indan-2-ylamide;
1-(4-amino-6,7-dimethoxy-quinazolin-2-yl)-4-benzyl-piperidine-4-carboxylic acid (1,2,3,4-tetrahydro-naphthalen-1-yl)-amide;
1-(4-amino-6,7-dimethoxy-quinazolin-2-yl)-4-benzyl-piperidine-4-carboxylic acid (1-hydroxy-indan-2-yl)-amide;
1-(4-amino-6,7-dimethoxy-quinazolin-2-yl)-4-benzyl-piperidine-4-carboxylic acid ((1S,2S)-2-hydroxy-indan-1-yl)-amide;
1-(4-amino-6,7-dimethoxy-quinazolin-2-yl)-4-benzyl-piperidine-4-carboxylic acid (1,2,3,4-tetrahydro-naphthalen-2-yl)-amide;
1-(4-amino-6,7-dimethoxy-quinazolin-2-yl)-4-benzyl-piperidine-4-carboxylic acid indan-1-yl amide;
4-benzyl-1-(4-hydroxy-6,7-dimethoxy-quinazolin-2-yl)-piperidine-4-carboxylic acid indan-2-ylamide;
4-benzyl-1-(4-hydroxy-6,7-dimethoxy-quinazolin-2-yl)-piperidine-4-carboxylic acid indan-2-yl-methyl-amide;
4-benzyl-1-(4-hydroxy-6,7-dimethoxy-quinazolin-2-yl)-piperidine-4-carboxylic acid (1,2,3,4-tetrahydro-naphthalen-2-yl)-amide;
4-benzyl-1-(4-hydroxy-6,7-dimethoxy-quinazolin-2-yl)-piperidine-4-carboxylic acid (5-chloro-1-hydroxy-indan-2-yl)-amide; and
4-benzyl-1-(4-hydroxy-6,7-dimethoxy-quinazolin-2-yl)-piperidine-4-carboxylic acid (1-hydroxy-1,2,3,4-tetrahydro-naphthalen-2-yl)-amide.

Preferred compounds of formula I are further those, wherein $R^3$ is —$(CH_2)_m$-aryl wherein m is 1 and one of $R^4$ or $R^5$ is —$(CR_2)_m$-aryl optionally substituted by $OCHF_2$, Cl, $N(CH_3)_2$ wherein m is 1, for example the following compounds
1-(4-amino-6,7-dimethoxy-quinazolin-2-yl)-4-benzyl-piperidine-4-carboxylic acid 4-difluoromethoxy-benzylamide;
1-(4-amino-6,7-dimethoxy-quinazolin-2-yl)-4-benzyl-piperidine-4-carboxylic acid [1-(4-chloro-phenyl)-ethyl]-amide;
1-(4-amino-6,7-dimethoxy-quinazolin-2-yl)-4-benzyl-piperidine-4-carboxylic acid 4-dimethylamino-benzylamide;
1-(4-amino-6,7-dimethoxy-quinazolin-2-yl)-4-benzyl-piperidine-4-carboxylic acid 3,4-dichloro-benzylamide;
1-(4-amino-6,7-dimethoxy-quinazolin-2-yl)-4-benzyl-piperidine-4-carboxylic acid (2-hydroxy-1-phenyl-ethyl)-amide;
1-(4-amino-6,7-dimethoxy-quinazolin-2-yl)-4-benzyl-piperidine-4-carboxylic acid ((R)-1-phenyl-ethyl)-amide; and
1-(4-amino-6,7-dimethoxy-quinazolin-2-yl)-4-benzyl-piperidine-4-carboxylic acid ((R)-1-phenyl-propyl)-amide.

Preferred compounds of formula I are further those, wherein $R^3$ is —$(CH_2)_m$-aryl wherein m is 1 and one of $R^4$ or $R^5$ is a heteroalkyl ring optionally substituted by phenyl, for example the following compound
[1-(4-amino-6,7-dimethoxy-quinazolin-2-yl)-4-benzyl-piperidin-4-yl]-(2-phenyl-pyrrolidin-1-yl)-methanone.

Preferred compounds of formula I are further those, wherein $R^3$ is $(CH_2)_m$-aryl wherein m is 1 and one of $R^4$ or $R^5$ is —$(CH_2)_m$-cycloalkyl wherein m is 0 or 1, for example the following compounds
4-benzyl-1-(4-hydroxy-6,7-dimethoxy-quinazolin-2-yl)-piperidine-4-carboxylic acid cyclopentylamide and
4-benzyl-1-(4-hydroxy-6,7-dimethoxy-quinazolin-2-yl)-piperidine-4-carboxylic acid cyclobutylmethyl-amide.

Preferred compounds of formula I are further those, wherein $R^3$ is lower alkyl and one of $R^4$ or $R^5$ is —$(CH_2)_m$-aryl wherein m is 1, for example the following compound
1-(4-amino-6,7-dimethoxy-quinazolin-2-yl)-4-isobutyl-piperidine-4-carboxylic acid benzylamide.

Preferred compounds of formula I are further those, wherein $R^3$ is —$(CH_2)_m$-cycloalkyl and one of $R^4$ or $R^5$ is —$(CH_2)_m$-aryl wherein m is 0 or 1, for example the following compounds
4-cyclopropylmethyl-1-(4-hydroxy-6,7-dimethoxy-quinazolin-2-yl)-piperidine-4-carboxylic acid benzylamide;
4-cyclopropylmethyl-1-(4-hydroxy-6,7-dimethoxy-quinazolin-2-yl)-piperidine-4-carboxylic acid benzyl-methyl-amide;
4-cyclobutylmethyl-1-(4-hydroxy-6,7-dimethoxy-quinazolin-2-yl)-piperidine-4-carboxylic acid benzylamide;
4-cyclobutylmethyl-1-(4-hydroxy-6,7-dimethoxy-quinazolin-2-yl)-piperidine-4-carboxylic acid benzyl-methyl-amide;
4-cyclobutylmethyl-1-(4-hydroxy-6,7-dimethoxy-quinazolin-2-yl)-piperidine-4-carboxylic acid (1,2,3,4-tetrahydro-naphthalen-2-yl)-amide; and
4-cyclobutylmethyl-1-(4-hydroxy-6,7-dimethoxy-quinazolin-2-yl)-piperidine-4-carboxylic acid indan-2-ylamide.

Preferred compounds of formula I are further those, wherein $R^3$ is —$(CH_2)_m$-cycloalkyl and one of $R^4$ or $R^5$ is —$(CH_2)_m$-cycloalkyl wherein m is 0, for example the following compound
4-cyclobutylmethyl-1-(4-hydroxy-6,7-dimethoxy-quinazolin-2-yl)-piperidine-4-carboxylic acid cyclopentylamide.

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process variant described below, which process comprises
a) coupling a compound of formula

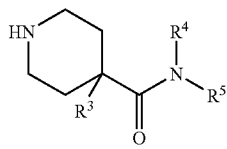

III with a compound of formula

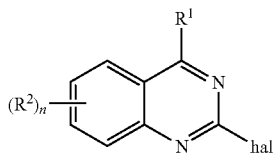

VIII to obtain a compound of formula

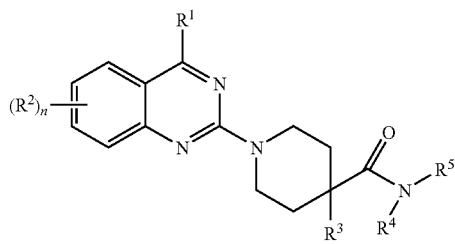

I wherein the groups $R^1$, $R^2$, $R^3$, $R^4$ and $R^5$ and the definition n are described above, and hal is halogen, and, if desired, converting the compounds obtained into pharmaceutically acceptable acid addition salts.

The preparation of compounds of formula I is further described in more detail in general scheme I and in examples 1-100.

As mentioned earlier, the compounds of formula I and their pharmaceutically usable addition salts possess valuable pharmacological properties. The compounds of the present invention are antagonists of neurokinin 3 (NK-3) receptors. The compounds were investigated in accordance with the tests given hereinafter.

EXPERIMENTAL PROCEDURE

The preparation of compounds of formula I of the present invention can be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

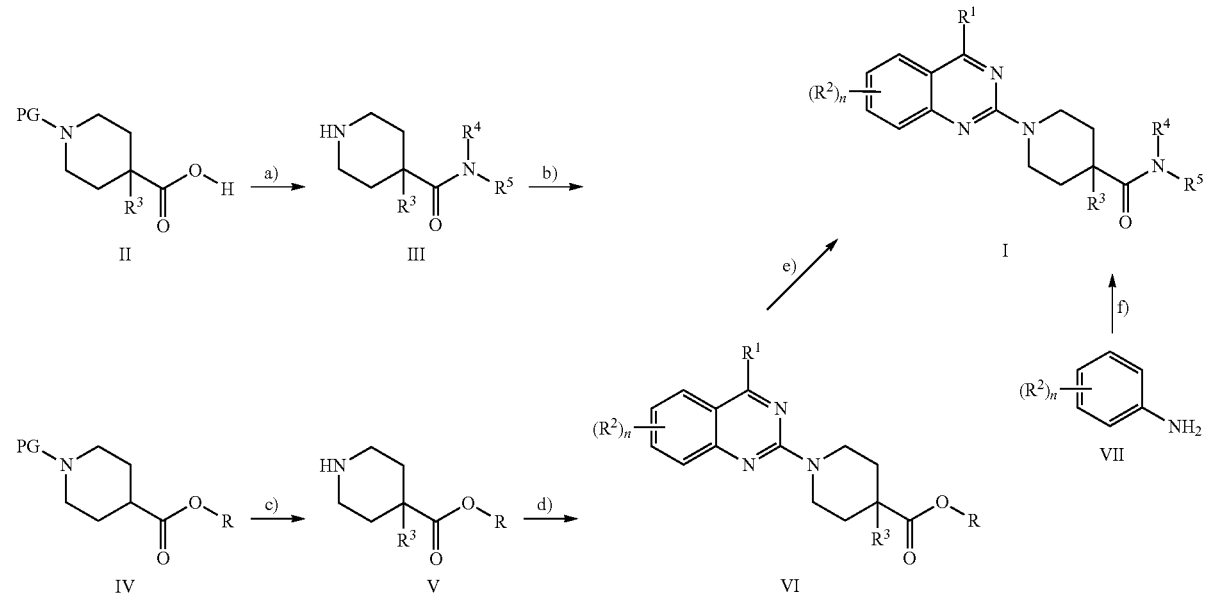

Step a)

Several N-protected piperidine-4-carboxylic acid derivatives (i.e. PG=Roc) II are commercially available or can be accessed by methods described in literature and can be transformed to their respective amide derivatives III by various methods as described in literature (for reaction conditions described in literature affecting such reactions see for example: Comprehensive Organic Transformations: A Guide to Functional Group Preparations, 2nd Edition, Richard C. Larock. John Wiley & Sons, New York, N.Y. 1999). However, it is convenient to couple the acid functionality with the respective amines under coupling conditions to the respective amide derivatives. The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The acid can conveniently be transformed to the respective amide through coupling with an amine (either commercially available or accessible by methods described in references or by methods known in the art; as appropriate) by employing the usage of coupling reagents. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. The reaction is conveniently carried out in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. The reaction conveniently can be carried out with heating from ambient temperature to reflux. The time required for the reaction may also vary widely, depending on many factors, notably the reaction temperature and the nature of the reagents. However, a period of 0.5 h to several days will usually suffice to yield the respective amide derivatives. The protecting group can be cleaved under various conditions, however it is convenient to cleave for instance a Boc protecting group under acidic conditions in the presence or the absence of a solvent. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the acid used in this stage, and any base commonly used in this type of reaction may equally be employed here. Examples of such acids include trifluoroacetic acid (TFA) and HCl, and the like. The reaction can take place over a wide range of temperatures, and the precise reaction temperature is not critical to the invention. The reaction conveniently is carried out with heating from ambient temperature to reflux. The time required for the reaction may also vary widely, depending on many factors, notably the reaction temperature and the nature of the reagents. However, a period of 0.5 h to several days will usually suffice to yield the respective amide derivatives III.

Step b)

Nucleophilic substitutions of heteroaromatic compounds are widely described in literature. For examples see also: Comprehensive Organic Transformations: A Guide to Functional Group Preparations, 2nd Edition, Richard C. Larock. John Wiley & Sons, New York, N.Y. 1999. It is convenient to transform amide derivatives III under basic conditions to the respective quinazoline derivatives I in the presence or the absence of a solvent. There is no particular restriction on the nature of the solvent to be employed, provided that it has no adverse effect on the reaction or the reagents involved and that it can dissolve the reagents, at least to some extent. Examples for suitable solvents include: Dimethylacetamide, DMF, dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. The reaction conveniently can be carried out with heating (even under microwave irradiation conditions) from ambient temperature to reflux. The time required for the reaction may also vary widely, depending on many factors, notably the reaction temperature and the nature of the reagents. However, a period of 0.5 h to several days will usually suffice to yield the respective quinazoline derivatives I.

Step c)

Several N-protected piperidine-4-carboxylic acid ester derivatives (i.e. PG=Boc) IV are commercially available or can be accessed by methods described in literature and can be transformed to their respective ester derivatives V by various methods as described in literature (for reaction conditions described in literature affecting such reactions see for example: Comprehensive Organic Transformations: A Guide to Functional Group Preparations, 2nd Edition, Richard C. Larock. John Wiley & Sons, New York, N.Y. 1999). However, it is convenient to deprotonate IV under basic conditions and react the intermediate with an electrophile R3-X in the presence of a solvent to access ester derivative V. There is no particular restriction on the nature of the solvent to be employed, provided that it has no adverse effect on the reaction or the reagents involved and that it can dissolve the reagents, at least to some extent. Examples for suitable solvents include: THF, diethyl ether and the like. There is no particular restriction on the nature of the base used in this stage, and any base commonly used in this type of reaction may equally be employed here. Examples of such bases include Butyl lithium and lithium diisopropylamide, and the like. Subsequent addition of an electrophile (R3-X) gives access to the respective N-protected ester derivative. The reaction can take place over a wide range of temperatures, and the precise reaction temperature is not critical to the invention. The reaction conveniently is carried out from −75° C. to reflux. The time required for the reaction may also vary widely, depending on many factors, notably the reaction temperature and the nature of the reagents. However, a period of 0.5 h to several days will usually suffice to yield the respective ester derivative. The protecting group can be cleaved under various conditions, however it is convenient to cleave for instance a Boc protecting group under acidic conditions in the presence or the absence of a solvent. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the acid used in this stage, and any base commonly used in this type of reaction may equally be employed here. Examples of such acids include trifluoroacetic acid (TFA) and HCl, and the like. The reaction can take place over a wide range of temperatures, and the precise reaction temperature is not critical to the invention. The reaction conveniently can be carried out with heating from ambient temperature to reflux. The time required for the reaction may also vary widely, depending on many factors, notably the reaction temperature and the nature of the reagents. However, a period of 0.5 h to several days will usually suffice to yield the respective ester derivatives V.

Step d)

Nucleophilic substitutions of heteroaromatic compounds are widely described in literature. For examples see also: Comprehensive Organic Transformations: A Guide to Functional Group Preparations, 2nd Edition, Richard C. Larock. John Wiley & Sons, New York, N.Y. 1999. It is convenient to transform ester derivatives V under basic conditions to the respective quinazoline derivatives VI in the presence or the absence of a solvent. There is no particular restriction on the nature of the solvent to be employed, provided that it has no adverse effect on the reaction or the reagents involved and that it can dissolve the reagents, at least to some extent. Examples for suitable solvents include: Dimethylacetamide, DMF, dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. The reaction conveniently can be carried out with heating (even under microwave irradiation conditions) from ambient temperature to reflux. The time required for the reaction may also vary widely, depending on many factors, notably the reaction temperature and the nature of the reagents. However, a period of 0.5 h to several days will usually suffice to yield the respective quinazoline derivatives VI.

Step e)

Transformation of ester derivative VI into the final quinazoline derivatives I can be done according to procedures described in literature. However, it is convenient to employ a two step reaction sequence in which the ester functionality in VI is cleaved under aqueous basic conditions and the liberated acid functionality converted with the respective amines under coupling conditions to the quinazoline derivatives I. The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The intermediately built acid can conveniently be transformed to the respective amide through coupling with an amine (either commercially available or accessible by methods described in references or by methods known in the art; as appropriate) by employing the usage of coupling reagents. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. The reaction conveniently can be carried out in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. The reaction conveniently can be carried out with heating from ambient temperature to reflux. The time required for the reaction may also vary widely, depending on many factors, notably the reaction temperature and the nature of the reagents. However, a period of 0.5 h to several days will usually suffice to yield quinazoline derivatives I.

Step f)

Aniline derivatives VII are commercially available or can be accessed by methods described in literature and can be transformed to their respective quinazoline derivatives I by methods as described in literature (J. Org. Chem. 2008, 73, 2473). It is convenient to react aniline derivatives VII with ethyl isocyanatoformate and subsequently with a suitable amide derivative III in the presence or the absence of a solvent and in the presence of a coupling reagent. Cyclisation is conveniently affected by TMS-Cl. There is no particular restriction on the nature of the solvent to be employed, provided that it has no adverse effect on the reaction or the reagents involved and that it can dissolve the reagents, at least to some extent. Examples for suitable solvents include: Dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like might be equally well employed to affect such transformation. The reaction can take place over a wide range of temperatures, and the precise reaction temperature is not critical to the invention. The reaction can conveniently be carried out with heating from ambient temperature to reflux. The time required for the reaction may also vary widely, depending on many factors, notably the reaction temperature and the nature of the reagents. However, a period of 0.5 h to several days will usually suffice to yield quinazoline derivatives I.

Experimental Part

Intermediate 1

4-Benzyl-piperidine-4-carboxylic acid (pyridin-3-ylmethyl)-amide; dihydrochloride

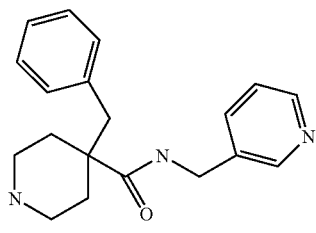

a) Step 1

4-Benzyl-4-[(pyridin-3-ylmethyl)-carbamoyl]-piperidine-1-carboxylic acid tert-butyl ester

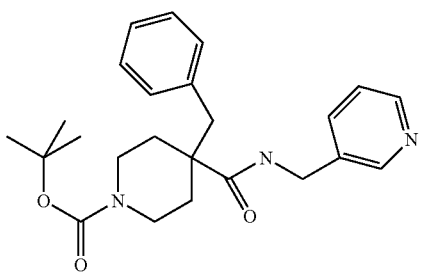

A mixture of 1.25 g (4 mmol) 4-Benzyl-piperidine-1,4-dicarboxylic acid mono-tert-butyl ester (commercially available), 1.5 g (4.6 mmol) TBTU, 3.37 mL (19 mmol) DIPEA and 0.508 g (4.7 mmol) 3-(aminomethyl)pyridine (commercially available) in 50 mL DMF was stirred at room temperature over night. The mixture was evaporated to dryness, taken up in DCM, absorbed on isolute and evaporated. The residue was purified by flash column chromatography on silica eluting with a gradient formed from DCM and 2N ammonia in methanol. The product containing fraction were evaporated to yield 1.55 g (97%) of the title compound as off-white foam. MS (m/e): 408.5 (MH+).

b) Step 2

A mixture of 1.55 g (3.78 mmol) 4-Benzyl-4-[(pyridin-3-ylmethyl)-carbamoyl]-piperidine-1-carboxylic acid tert-butyl ester and 2.9 mL trifluoroacetic acid in 100 mL DCM was stirred at 0° C. over night. 30 mL 4N NaOH was added and the mixture was extracted with DCM. The combined organic layers were washed with brine, dried with Na$_2$SO$_4$ and evaporated to dryness. The oily residue was treated with diethyl ether and 2N HCl in diethyl ether was added. The mixture was evaporated to dryness to yield 1.3 g (90%) of the title compound as off-white foam. MS (m/e): 202.4/310.4 (MH+).

Intermediate 2

4-(4-Chloro-benzyl)-piperidine-4-carboxylic acid benzylamide

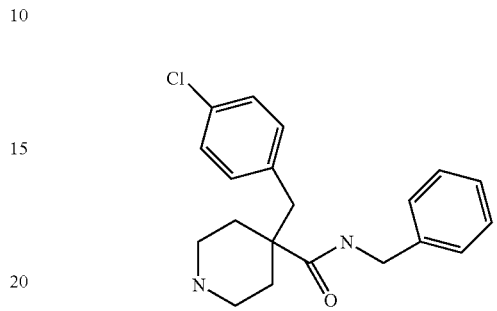

In analogy to the procedure described for the synthesis of 4-benzyl-piperidine-4-carboxylic acid (pyridin-3-ylmethyl)-amide; hydrochloride (intermediate 1) the title compound was prepared from 4-(4-chloro-benzyl)-piperidine-1,4-dicarboxylic acid mono-tert-butyl ester (commercially available) and benzylamine (commercially available) with subsequent cleavage of the protecting group under acidic conditions. The title compound was purified on silica eluting with a gradient formed from DCM and 2N NH$_3$ and methanol. MS (m/e): 236.1/343.2 (MH+).

Intermediate 3

4-(4-Fluoro-benzyl)-piperidine-4-carboxylic acid benzylamide

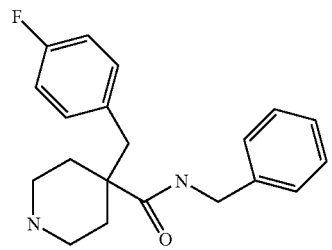

In analogy to the procedure described for the synthesis of 4-benzyl-piperidine-4-carboxylic acid (pyridin-3-ylmethyl)-amide; hydrochloride (intermediate 1) the title compound was prepared from 4-(4-fluoro-benzyl)-piperidine-1,4-dicarboxylic acid mono-tert-butyl ester (commercially available) and benzylamine (commercially available) with subsequent cleavage of the protecting group under acidic conditions. The title compound was purified on silica eluting with a gradient formed from DCM and 2N NH$_3$ and methanol. MS (m/e): 220.2/327.2 (MH+).

Intermediate 4

4-(4-Chloro-benzyl)-piperidine-4-carboxylic acid 2-chloro-benzylamide

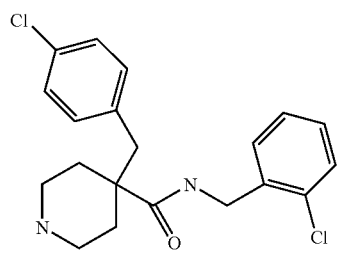

In analogy to the procedure described for the synthesis of 4-benzyl-piperidine-4-carboxylic acid (pyridin-3-ylmethyl)-amide; hydrochloride (intermediate 1) the title compound was prepared from 4-(4-chloro-benzyl)-piperidine-1,4-dicarboxylic acid mono-tert-butyl ester (commercially available) and 2-chloro-benzylamine (commercially available) with subsequent cleavage of the protecting group under acidic conditions. The title compound was purified on silica eluting with a gradient formed from DCM and methanol and the free base was liberated under basic conditions. MS (m/e): 377.1 (MH$^+$).

Intermediate 5

2,7-Dichloro-6-fluoro-quinazolin-4-ol

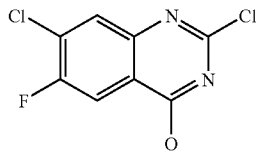

A mixture of 334 mg (1.33 mmol) 2,4,7-Trichloro-6-fluoro-quinazoline (WO9532205) and 6.6 mL 1N NaOH aq. in 2 mL THF was stirred for 2 h at room temperature. The pH of the mixture was adjusted to pH=4-5 with acetic acid. The precipitate was filtered of to yield the title compound which was used in the consecutive step without further purification.

Example 1

1-(4-Amino-6,7-dimethoxy-quinazolin-2-yl)-4-benzyl-piperidine-4-carboxylic acid (pyridin-3-ylmethyl)-amide

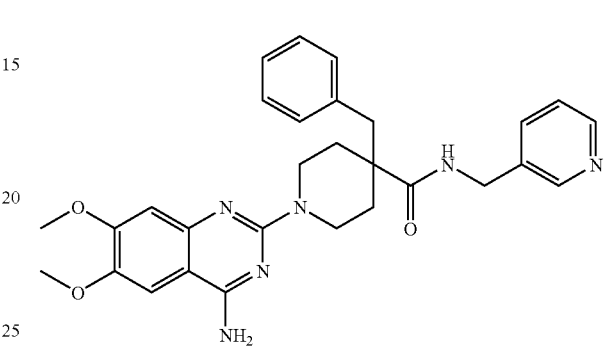

A mixture of 12 mg (0.05 mmol) 4-amino-2-chloro-6,7-dimethoxyquinazoline (commercially available), 28.6 mg (0.074 mmol) 4-benzyl-piperidine-4-carboxylic acid (pyridin-3-ylmethyl)-amide; dihydrochloride (intermediate 1) and 32 mg (0.25 mmol) DIPEA in 0.8 mL dimethylacetamide was heated in a microwave oven for 20 min to 190° C. The mixture was subjected to purification by preparative HPLC on reversed phase eluting with a gradient formed from acetonitrile, water and acetic acid to yield after evaporation of the product fractions 5.7 mg (21%) of the title compound as light brown solid. MS (m/e): 513.4 (MH$^+$).

In analogy to the procedure described for the synthesis of 1-(4-Amino-6,7-dimethoxy-quinazolin-2-yl)-4-benzyl-piperidine-4-carboxylic acid (pyridin-3-ylmethyl)-amide (example 1) further quinazoline derivatives have been synthesized from their respective starting materials as mentioned in table 1. Table 1 comprises example 2-17.

TABLE 1

| NO | structure | Systematic Name | starting materials | MW MH+ found |
|---|---|---|---|---|
| 1 | 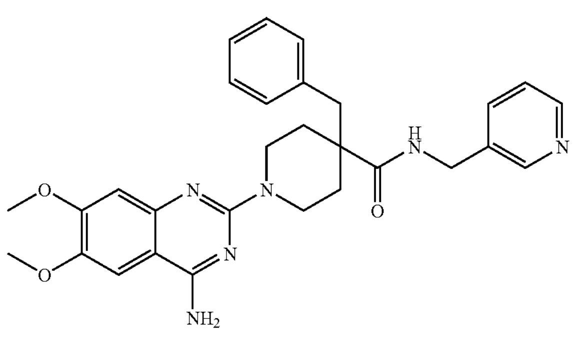 | 1-(4-Amino-6,7-dimethoxy-quinazolin-2-yl)-4-benzyl-piperidine-4-carboxylic acid (pyridin-3-ylmethyl)-amide | 2-Chloro-6,7-dimethoxy-4-quinazolinamine (commercially available) and 4-Benzyl-piperidine-4-carboxylic acid (pyridin-3-ylmethyl)-amide, hydrochloride (intermediate 1) | 513.4 |

TABLE 1-continued

| NO | structure | Systematic Name | starting materials | MW MH+ found |
|----|-----------|-----------------|--------------------|--------------|
| 2 | 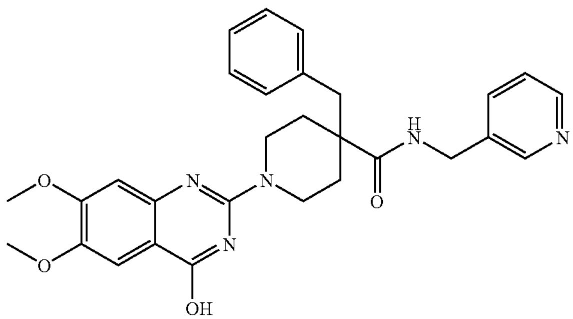 | 4-Benzyl-1-(4-hydroxy-6,7-dimethoxy-quinazolin-2-yl)-piperidine-4-carboxylic acid (pyridin-3-ylmethyl)-amide | 2-Chloro-4,6,7-trimethoxyquinazoline (Bioorganic & Medicinal Chemistry 2005, 13, 3681) and 4-Benzyl-piperidine-4-carboxylic acid (pyridin-3-ylmethyl)-amide (intermediate 1) | 514.4 |
| 3 | 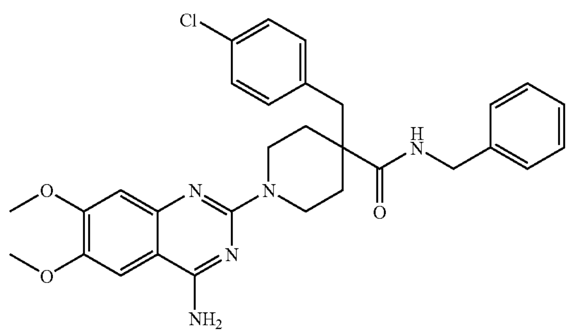 | 1-(4-Amino-6,7-dimethoxy-quinazolin-2-yl)-4-(4-chloro-benzyl)-piperidine-4-carboxylic acid benzylamide | 2-Chloro-6,7-dimethoxy-4-quinazolinamine (commercially available) and 4-(4-Chloro-benzyl)-piperidine-4-carboxylic acid benzylamide (intermediate 2) | 546.3 |
| 4 | 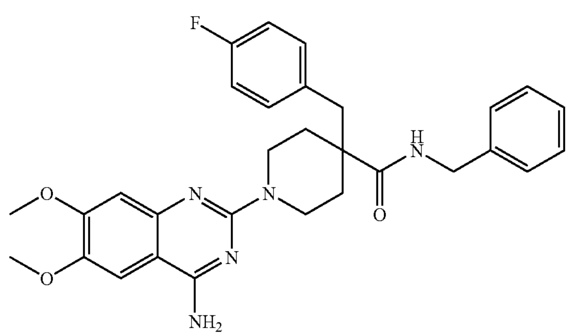 | 1-(4-Amino-6,7-dimethoxy-quinazolin-2-yl)-4-(4-fluoro-benzyl)-piperidine-4-carboxylic acid benzylamide | 2-Chloro-6,7-dimethoxy-4-quinazolinamine (commercially available) and 4-(4-Fluoro-benzyl)-piperidine-4-carboxylic acid benzylamide (intermediate 3) | 530.2 |
| 5 | 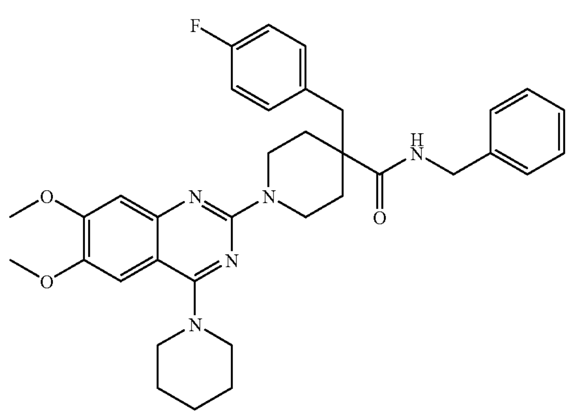 | 1-(6,7-Dimethoxy-4-piperidin-1-yl-quinazolin-2-yl)-4-(4-fluoro-benzyl)-piperidine-4-carboxylic acid benzylamide | 2-chloro-6,7-dimethoxy-4-(1-piperidinyl)quinazoline (commercially available) and 4-(4-Fluoro-benzyl)-piperidine-4-carboxylic acid benzylamide (intermediate 3) | 598.4 |

TABLE 1-continued

| NO | structure | Systematic Name | starting materials | MW MH+ found |
|---|---|---|---|---|
| 6 | 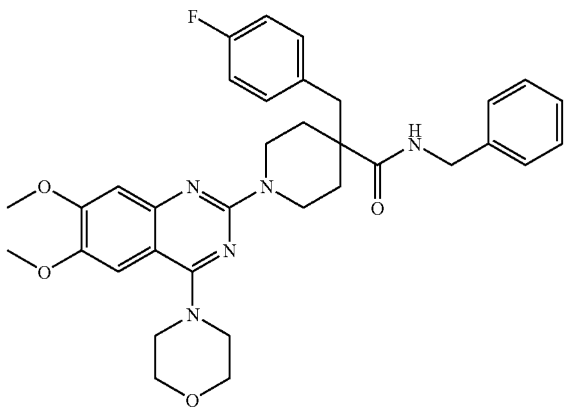 | 1-(6,7-Dimethoxy-4-morpholin-4-yl-quinazolin-2-yl)-4-(4-fluoro-benzyl)-piperidine-4-carboxylic acid benzylamide | 2-chloro-6,7-dimethoxy-4-(4-morpholinyl)quinazoline (commercially available) and 4-(4-Fluoro-benzyl)-piperidine-4-carboxylic acid benzylamide (intermediate 3) | 600.4 |
| 7 | 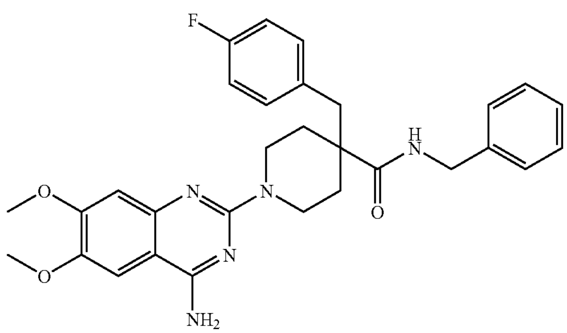 | 1-(4-Amino-7-chloro-quinazolin-2-yl)-4-(4-fluoro-benzyl)-piperidine-4-carboxylic acid benzylamide | 2,7-Dichloro-4-quinazolinamine (commercially available) and 4-(4-Fluoro-benzyl)-piperidine-4-carboxylic acid benzylamide (intermediate 3) | 504.2 |
| 8 | 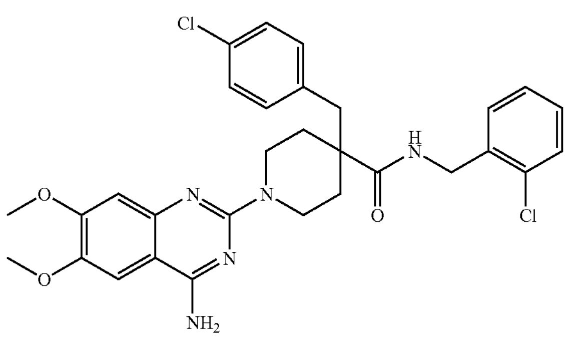 | 1-(4-Amino-6,7-dimethoxy-quinazolin-2-yl)-4-(4-chloro-benzyl)-piperidine-4-carboxylic acid 2-chloro-benzylamide | 2-Chloro-6,7-dimethoxy-4-quinazolinamine (commercially available) and 4-(4-Chloro-benzyl)-piperidine-4-carboxylic acid 2-chloro-benzylamide (intermediate 4) | 580.2 |
| 9 | 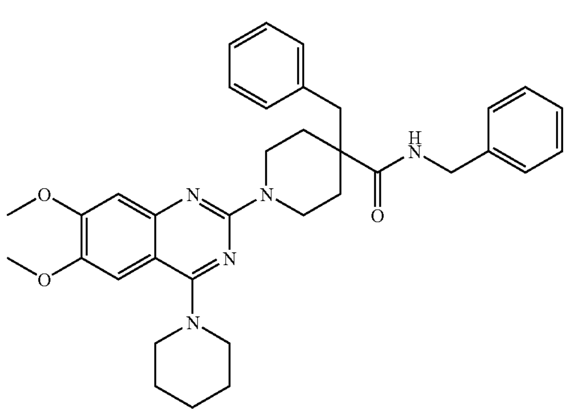 | 4-Benzyl-1-(6,7-dimethoxy-4-piperidin-1-yl-quinazolin-2-yl)-piperidine-4-carboxylic acid benzylamide | 2-chloro-6,7-dimethoxy-4-(1-piperidinyl)quinazoline (commercially available) and 4-Benzyl-piperidine-4-carboxylic acid benzylamide (WO2003088908) | 580.4 |

TABLE 1-continued

| NO | structure | Systematic Name | starting materials | MW MH+ found |
|---|---|---|---|---|
| 10 | 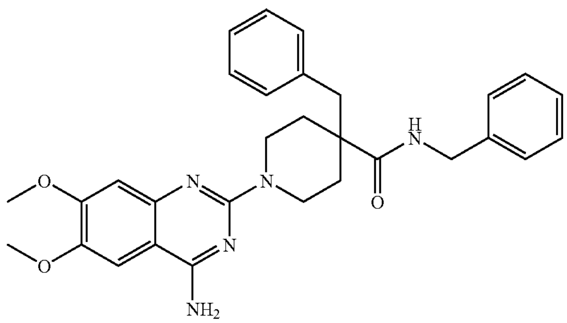 | 1-(4-Amino-6,7-dimethoxy-quinazolin-2-yl)-4-benzyl-piperidine-4-carboxylic acid benzylamide | 2-Chloro-6,7-dimethoxy-4-quinazolinamine (commercially available) and 4-Benzyl-piperidine-4-carboxylic acid benzylamide (WO2003088908) | 512.5 |
| 11 | 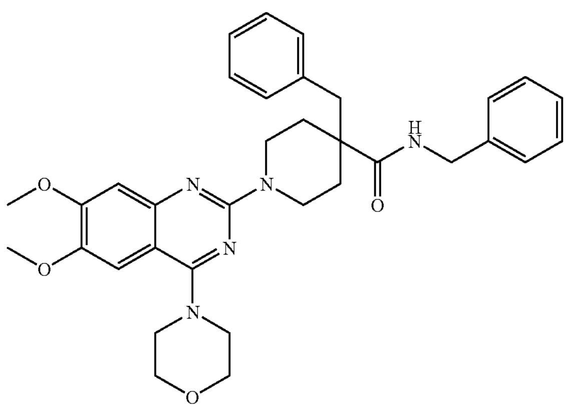 | 4-Benzyl-1-(6,7-dimethoxy-4-morpholin-4-yl-quinazolin-2-yl)-piperidine-4-carboxylic acid benzylamide | 2-chloro-6,7-dimethoxy-4-(4-morpholinyl)quinazoline (commercially available) and 4-Benzyl-piperidine-4-carboxylic acid benzylamide (WO2003088908) | 582.3 |
| 12 | 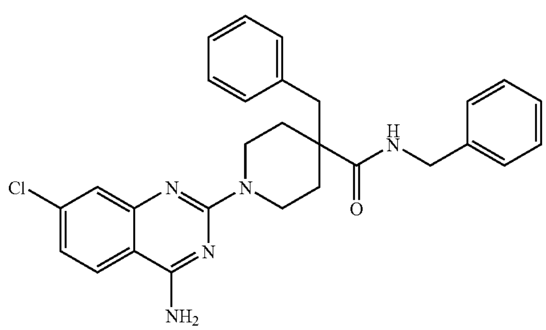 | 1-(4-Amino-7-chloro-quinazolin-2-yl)-4-benzyl-piperidine-4-carboxylic acid benzylamide | 2,7-Dichloro-4-quinazolinamine (commercially available) and 4-Benzyl-piperidine-4-carboxylic acid benzylamide (WO2003088908) | 486.4 |
| 13 | 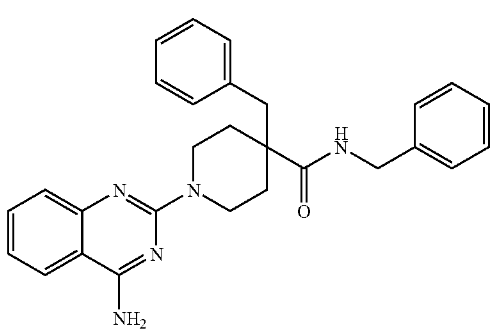 | 1-(4-Amino-quinazolin-2-yl)-4-benzyl-piperidine-4-carboxylic acid benzylamide | 2-Chloro-4-aminoquinazoline (commercially available) and 4-Benzyl-piperidine-4-carboxylic acid benzylamide (WO2003088908) | 452.2 |

TABLE 1-continued

| NO | structure | Systematic Name | starting materials | MW MH+ found |
|----|-----------|-----------------|--------------------|--------------|
| 14 | 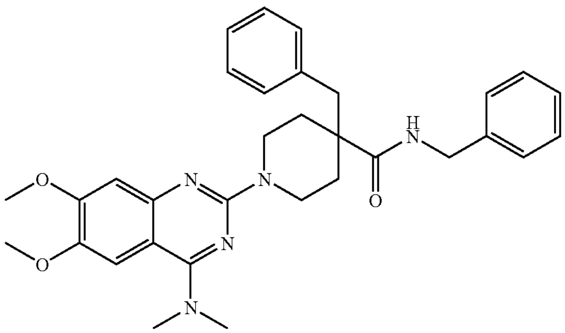 | 4-Benzyl-1-(4-dimethylamino-6,7-dimethoxy-quinazolin-2-yl)-piperidine-4-carboxylic acid benzylamide | 2-Chloro-6,7-dimethoxy-N,N-dimethyl-4-quinazolinamine (commercially available) and 4-Benzyl-piperidine-4-carboxylic acid benzylamide (WO2003088908) | 540.4 |
| 15 | 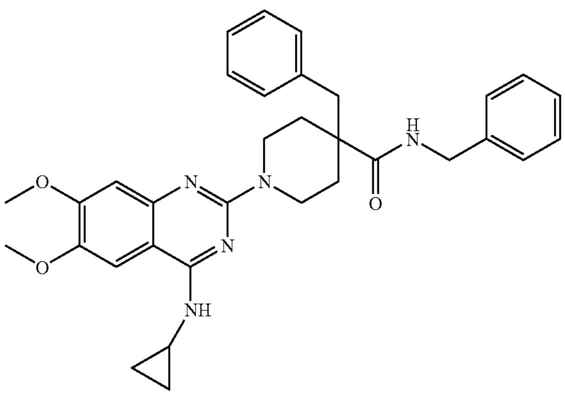 | 4-Benzyl-1-(4-cyclopropylamino-6,7-dimethoxy-quinazolin-2-yl)-piperidine-4-carboxylic acid benzylamide | 2-chloro-N-cyclopropyl-6,7-dimethoxy-4-quinazolinamine (commercially available) and 4-Benzyl-piperidine-4-carboxylic acid benzylamide (WO2003088908) | 552.2 |
| 16 | 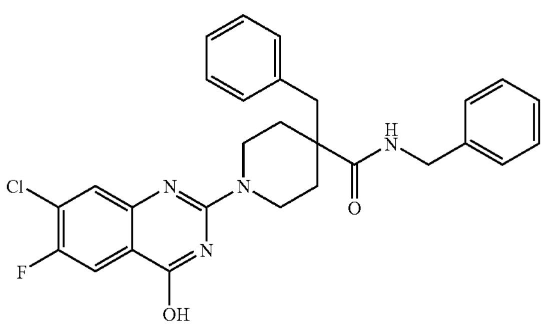 | 4-Benzyl-1-(7-chloro-6-fluoro-4-hydroxy-quinazolin-2-yl)-piperidine-4-carboxylic acid benzylamide | 2,7-Dichloro-6-fluoro-quinazolin-4-ol (intermediate 5) and 4-Benzyl-piperidine-4-carboxylic acid benzylamide (WO2003088908) | 505.1 |
| 17 | 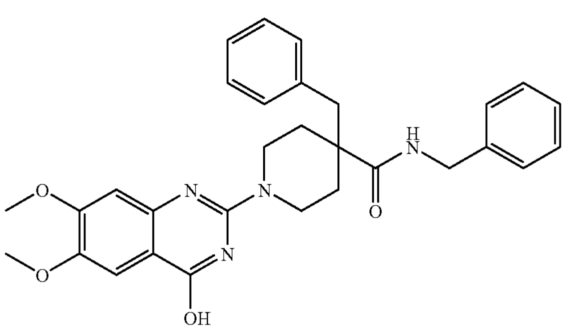 | 4-Benzyl-1-(4-hydroxy-6,7-dimethoxy-quinazolin-2-yl)-piperdine-4-carboxylic acid benzylamide | 2-Chloro-6,7-dimethoxy-3H-quinazolin-4-one (commercially available) and 4-Benzyl-piperidine-4-carboxylic acid benzylamide (WO2003088908) | 513.4 |

Example 18

1-(4-Amino-6,7-dimethoxy-quinazolin-2-yl)-4-benzyl-piperidine-4-carboxylic acid ((S)-1-phenyl-propyl)-amide

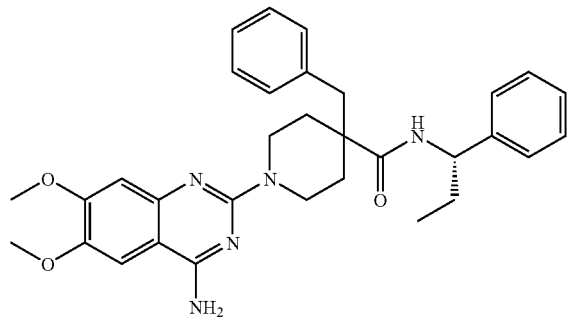

a) Step 1

1-(4-Amino-6,7-dimethoxy-quinazolin-2-yl)-4-benzyl-piperidine-4-carboxylic acid

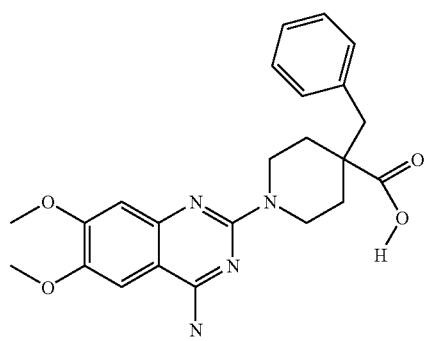

A mixture of 2 g (8.3 mmol) 4-amino-2-chloro-6,7-dimethoxyquinazoline, 2.37 g (9.6 mmol) 4-(Ethoxycarbonyl)-4-phenylpiperidine and 7.2 mL (42 mmol) DIPEA in 50 mL N,N-dimethylacetamide was heated in a microwave oven for 45 min to 190° C. The mixture was evaporated to dryness taken up on isolute and subjected to purification by column chromatography on silica eluting with a gradient formed from DCM, methanol and 2N $NH_3$ to yield after evaporation the intermediate ester. The residue was taken up in 50 mL ethanol and 10 mL 4N NaOH and warmed to reflux for 52 h. Water and ethyl acetate was added after evaporation of ethanol and the vigorously stirred mixture was adjusted to pH 4-5 with acetic acid. The precipitate was filtered off, washed with water and methanol and dried under vacuum to yield 2.65 g (75%) of the title compound as off-white solid. MS (m/e): 423.2 (MH$^+$).

b) Step 2

A mixture of 21 mg (0.05 mmol) 1-(4-Amino-6,7-dimethoxy-quinazolin-2-yl)-4-benzyl-piperidine-4-carboxylic acid, 7 mg (0.06 mmol) (S)-1-phenyl-propyl-amine, 20 mg (0.052 mmol) HATU and 50 uL (0.3 mmol) DIPEA in 1 mL DMF was shaken at room temperature over night. The mixture was subjected to purification by preparative HPLC on reversed phase eluting with a gradient formed from acetonitrile, water and formic acid to yield after evaporation of the product fractions 22 mg (86%) of the title compound as off-white solid. MS (m/e): 540.4 (MH$^+$).

Intermediate 6

4-Benzyl-1-(4-hydroxy-6,7-dimethoxy-quinazolin-2-yl)-piperidine-4-carboxylic acid

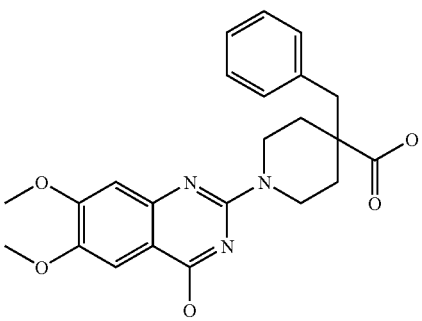

a) Step 1

4-Benzyl-1-(4-hydroxy-6,7-dimethoxy-quinazolin-2-yl)-piperidine-4-carboxylic acid ethyl ester

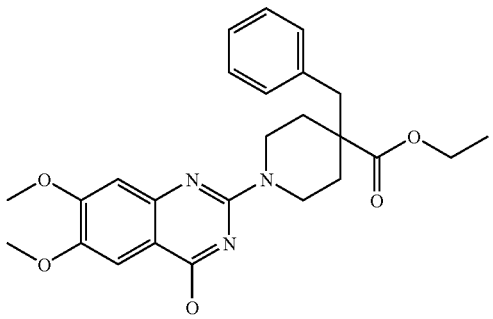

A mixture of 1.2 g (5 mmol) 2-Chloro-6,7-dimethoxy-quinazolin-4-ol (commercially available), 2.26 g (8 mmol) 4-Benzyl-piperidine-4-carboxylic acid ethyl ester; hydrochloride and 1.93 g (15 mmol) DIPEA in 80 mL ethanol was heated to reflux for 62 h. The mixture was concentrated, the precipitate filtered off and washed with ethanol and diethyl ether. The residue was dried. 1.9 g (87%) of the title compound was isolated as white solid. MS (m/e): 452.2 (MH$^+$).

b) Step 2

A mixture of 1.9 g (4.2 mmol) 4-Benzyl-1-(4-hydroxy-6,7-dimethoxy-quinazolin-2-yl)-piperidine-4-carboxylic acid ethyl ester and 21 mL 4N NaOH aq. in 50 mL ethanol was heated to reflux over night. After concentration water was added and acetic acid to pH=4-5. HCl was added to adjust to pH=2. The precipitate was filtered off, washed with water, ethanol and diethyl ether. The residue was dried under vacuum at 60° C. to yield 1.75 g (98%) of the title compound as white solid. MS (m/e): 422.1 (M−H$^+$).

Intermediate 7

1-(4-Amino-6,7-dimethoxy-quinazolin-2-yl)-4-isobutyl-piperidine-4-carboxylic acid

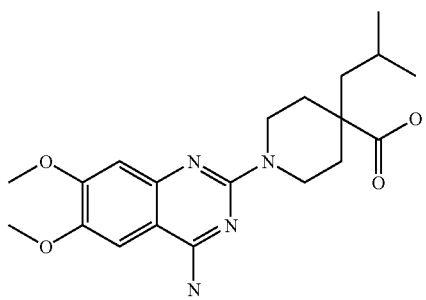

a) Step 1

4-Isobutyl-piperidine-1,4-dicarboxylic acid 1-tert-butyl ester 4-ethyl ester

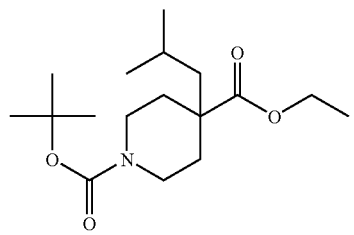

4.7 g (47 mmol) DIPEA in THF at −5° C. was treated slowly with 29.1 mL (47 mmol) n-Buli (1.6N in hexane) and stirred for 30 min at −5° C. and subsequently cooled to −75° C. and stirred for 2 h. A solution of 10 g (39 mmol) ethyl 1-tert-butoxycarbonylpiperidine-4-carboxylate (commercially available) in THF was added and the mixture was stirred for 2 h at −75° C. 8.51 g (47 mmol) 1-iodo-2-methyl-propane was added and the mixture was allowed to stir to room temperature over night. The mixture was quenched at 0° C. with citric acid 10% aq. and extracted with ethyl acetate. The combined organic layers were washed with NaCl aq. sat., dried with Na$_2$SO$_4$, filtered and evaporated. The residue was purified by column chromatography on silica eluting with a gradient formed heptane and t-butyl-methylether. The combined product fractions were evaporated to yield 10.2 g (84%) of the title compound as light yellow oil. MS (m/e): 331.2 (M+NH$_4^+$).

b) Step 2

4-Isobutyl-piperidine-4-carboxylic acid ethyl ester; hydrochloride

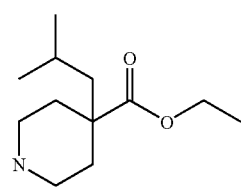

A mixture of 4.56 g (15 mmol) 4-Isobutyl-piperidine-1,4-dicarboxylic acid 1-tert-butyl ester 4-ethyl ester and 36 mL 4N HCl in 60 mL dioxane was stirred at room temperature over night. The mixture was evaporated to dryness and titurated with diethyl ether. The precipitate was filtered, washed with diethyl ether and dried under vacuum at 40° C. to yield 3.47 g (95%) of the title compound as white solid. MS (m/e): 214.3 (M+H$^+$).

c) Step 3

In analogy to the procedure described for the synthesis of 4-Benzyl-1-(4-hydroxy-6,7-dimethoxy-quinazolin-2-yl)-piperidine-4-carboxylic acid (intermediate 6) the title compound was prepared from 2-Chloro-6,7-dimethoxy-quinazolin-4-ol (commercially available) and 4-Isobutyl-piperidine-4-carboxylic acid ethyl ester; hydrochloride with subsequent saponification of the ethyl ester with NaOH aq. as white solid. MS (m/e): 389.1 (M+H$^+$).

Intermediate 8

4-Cyclopropylmethyl-1-(4-hydroxy-6,7-dimethoxy-quinazolin-2-yl)-piperidine-4-carboxylic acid

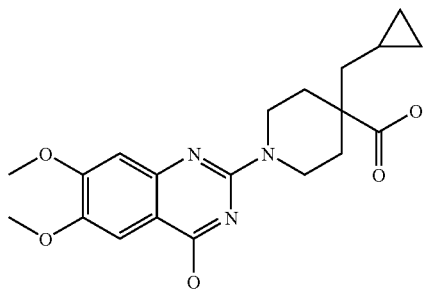

a) Step 1

4-Cyclopropylmethyl-piperidine-1,4-dicarboxylic acid 1-tert-butyl ester 4-ethyl ester

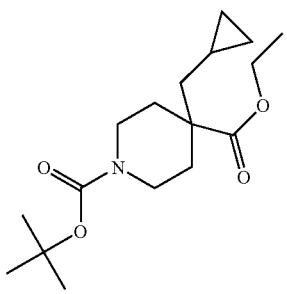

In analogy to the procedure described for the synthesis of 4-Isobutyl-piperidine-1,4-dicarboxylic acid 1-tert-butyl ester 4-ethyl ester the title compound was prepared from ethyl 1-tert-butoxycarbonylpiperidine-4-carboxylate (commercially available) and cyclopropylmethyl bromide. MS (m/e): 312.2 (M+H⁺)

b) Step 2

4-Cyclopropylmethyl-piperidine-4-carboxylic acid ethyl ester; hydrochloride

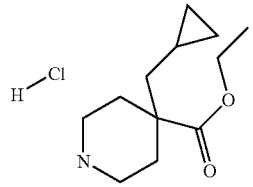

In analogy to the procedure described for the synthesis of 4-Isobutyl-piperidine-4-carboxylic acid ethyl ester; hydrochloride the title compound was prepared from 4-Cyclopropylmethyl-piperidine-1,4-dicarboxylic acid 1-tert-butyl ester 4-ethyl ester. MS (m/e): 212.2 (M+H⁺)

c) Step 3

A mixture of 0.9 g (3.74 mmol) 2-Chloro-6,7-dimethoxy-quinazolin-4-ol (commercially available), 1.52 g (6.15 mmol) 4-Cyclopropylmethyl-piperidine-4-carboxylic acid ethyl ester; hydrochloride and 1.48 g (11.4 mol) DIPEA in 70 mL ethanol was heated to reflux. The mixture was concentrated, the precipitate filtered off, washed with ethanol and diethyl ether to obtain after drying 1.25 g (78%) of 4-Cyclopropylmethyl-1-(4-hydroxy-6,7-dimethoxy-quinazolin-2-yl)-piperidine-4-carboxylic acid ethyl ester as off-white crystals. The ester was taken up in 50 mL ethanol and 22.5 mL NaOH aq. (4N) was added and heated to reflux. The mixture was concentrated and acidified with acetic acid and HCl aq. the precipitate was filtered off, washed with water, ethanol and diethyl ether and dried to yield 1 g of the title compound as white crystals. MS (m/e): 388.3 (M+H⁺)

Intermediate 9

4-Cyclobutylmethyl-1-(4-hydroxy-6,7-dimethoxy-quinazolin-2-yl)-piperidine-4-carboxylic acid

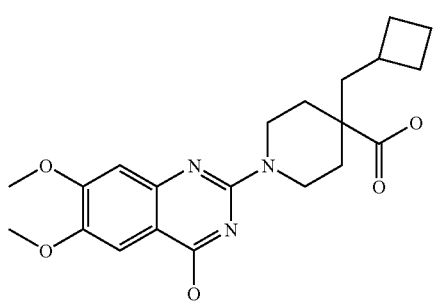

a) Step 1

4-Cyclobutylmethyl-piperidine-1,4-dicarboxylic acid 1-tert-butyl ester-4-ethyl ester

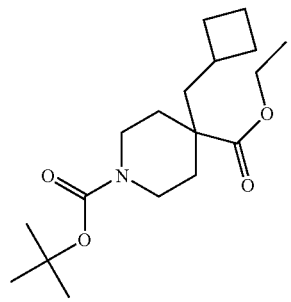

In analogy to the procedure described for the synthesis of 4-Isobutyl-piperidine-1,4-dicarboxylic acid 1-tert-butyl ester 4-ethyl ester the title compound was prepared from ethyl 1-tert-butoxycarbonylpiperidine-4-carboxylate (commercially available) and cyclobutylmethyl bromide. MS (m/e): 326.3 (M+H⁺)

b) Step 2

4-Cyclobutylmethyl-piperidine-4-carboxylic acid ethyl ester; hydrochloride

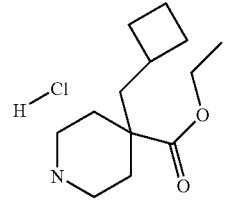

In analogy to the procedure described for the synthesis of 4-Isobutyl-piperidine-4-carboxylic acid ethyl ester, hydrochloride the title compound was prepared from 4-Cyclobutylmethyl-piperidine-1,4-dicarboxylic acid 1-tert-butyl ester-4-ethyl ester. MS (m/e): 226.3 (M+H⁺)

c) Step 3

In analogy to the procedure described for the synthesis of 4-Cyclobutylmethyl-1-(4-hydroxy-6,7-dimethoxy-quinazolin-2-yl)-piperidine-4-carboxylic acid (intermediate 9) the title compound was prepared from 2-Chloro-6,7-dimethoxy-quinazolin-4-ol (commercially available) and 4-Cyclobutyl-methyl-piperidine-4-carboxylic acid ethyl ester; hydrochloride with subsequent saponification of the ester functionality with NaOH aq. (4N). MS (m/e): 402.4 (M+H⁺)

In analogy to the procedure described for the synthesis of 1-(4-Amino-6,7-dimethoxy-quinazolin-2-yl)-4-benzyl-piperidine-4-carboxylic acid ((S)-1-phenyl-propyl)-amide (example 18) further quinazoline derivatives have been synthesized from their respective starting materials as mentioned in table 2. Table 2 comprises example 19-80.

TABLE 2

| No | Structure | Systematic name | Starting materials | MW MH+ found |
|---|---|---|---|---|
| 18 | 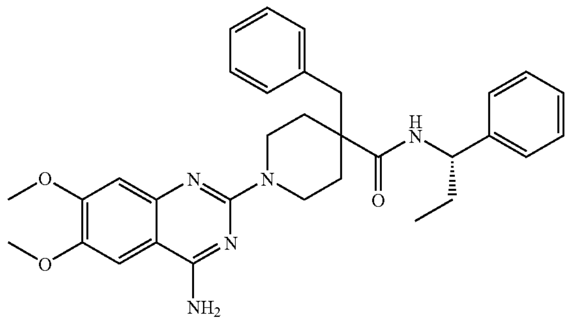 | 1-(4-Amino-6,7-dimethoxy-quinazolin-2-yl)-4-benzyl-piperidine-4-carboxylic acid ((S)-1-phenyl-propyl)-amide | 1-(4-Amino-6,7-dimethoxy-quinazolin-2-yl)-4-benzyl-piperidine-4-carboxylic acid and (S)-1-phenyl-propyl)-amine (commercially available) | 540.4 |
| 19 | 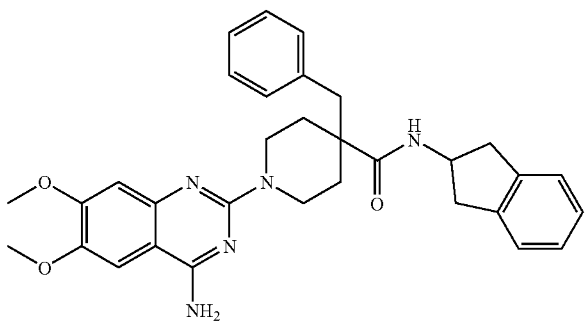 | 1-(4-Amino-6,7-dimethoxy-quinazolin-2-yl)-4-benzyl-piperidine-4-carboxylic acid indan-2-ylamie | 1-(4-Amino-6,7-dimethoxy-quinazolin-2-yl)-4-benzyl-piperidine-4-carboxylic acid and indan-2-ylamine (commercially available) | 538.4 |
| 20 | 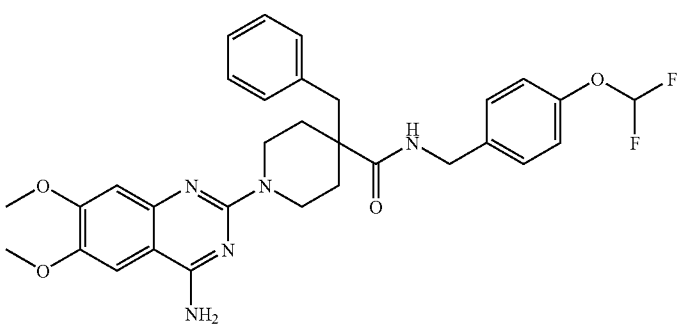 | 1-(4-Amino-6,7-dimethoxy-quinazolin-2-yl)-4-benzyl-piperidine-4-carboxylic acid 4-difluoromethoxy-benzylamide | 1-(4-Amino-6,7-dimethoxy-quinazolin-2-yl)-4-benzyl-piperidine-4-carboxylic acid and 4-difluoromethoxy-benzylamine (commercially available) | 578.4 |
| 21 | 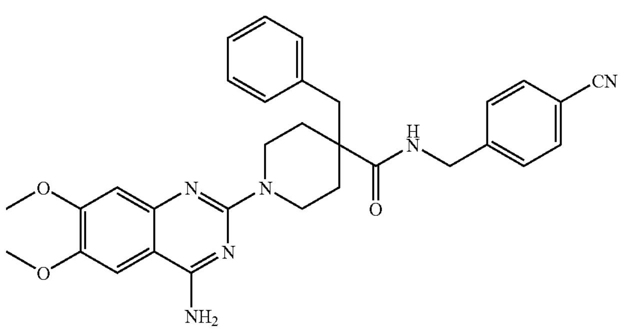 | 1-(4-Amino-6,7-dimethoxy-quinazolin-2-yl)-4-benzyl-piperidine-4-carboxylic acid 4-cyano-benzylamide | 1-(4-Amino-6,7-dimethoxy-quinazolin-2-yl)-4-benzyl-piperidine-4-carboxylic acid and 4-cyano-benzylamine (commercially available) | 537.4 |

TABLE 2-continued

| No | Structure | Systematic name | Starting materials | MW MH+ found |
|---|---|---|---|---|
| 22 | 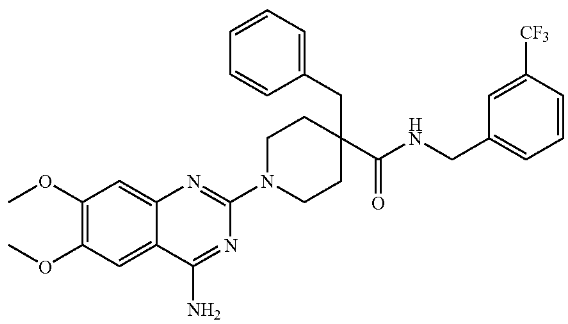 | 1-(4-Amino-6,7-dimethoxy-quinazolin-2-yl)-4-benzyl-piperidine-4-carboxylic acid 3-trifluoromethyl-benzylamide | 1-(4-Amino-6,7-dimethoxy-quinazolin-2-yl)-4-benzyl-piperidine-4-carboxylic acid and 3-trifluoromethyl-benzylamine (commercially available) | 580.4 |
| 23 | 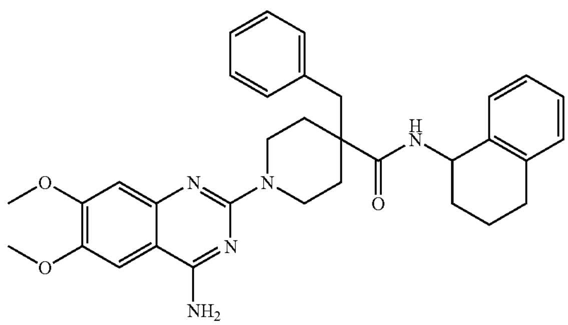 | 1-(4-Amino-6,7-dimethoxy-quinazolin-2-yl)-4-benzyl-piperidine-4-carboxylic acid (1,2,3,4-tetrahydro-naphthalen-1-yl)-amide | 1-(4-Amino-6,7-dimethoxy-quinazolin-2-yl)-4-benzyl-piperidine-4-carboxylic acid and (1,2,3,4-tetrahydro-naphthalen-1-yl)-amine (commercially available) | 552.5 |
| 24 | 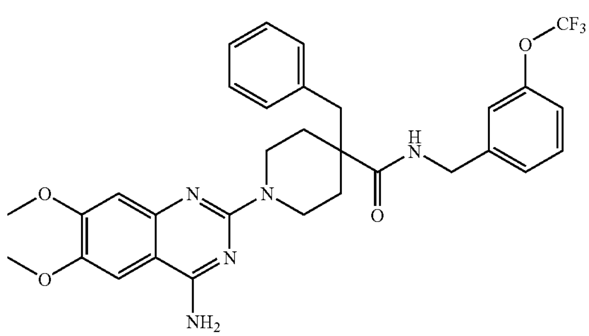 | 1-(4-Amino-6,7-dimethoxy-quinazolin-2-yl)-4-benzyl-piperidine-4-carboxylic acid 3-trifluoromethoxy-benzylamide | 1-(4-Amino-6,7-dimethoxy-quinazolin-2-yl)-4-benzyl-piperidine-4-carboxylic acid and 3-trifluoromethoxy-benzylamine (commercially available) | 596.4 |
| 25 | 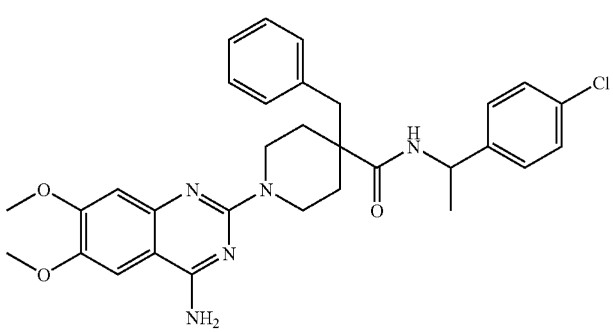 | 1-(4-Amino-6,7-dimethoxy-quinazolin-2-yl)-4-benzyl-piperidine-4-carboxylic acid [1-(4-chloro-phenyl)-ethyl]-amide | 1-(4-Amino-6,7-dimethoxy-quinazolin-2-yl)-4-benzyl-piperidine-4-carboxylic acid and 1-(4-chloro-phenyl)-ethyl]-amine (commercially available) | 560.3 |

TABLE 2-continued

| No | Structure | Systematic name | Starting materials | MW MH+ found |
|---|---|---|---|---|
| 26 | 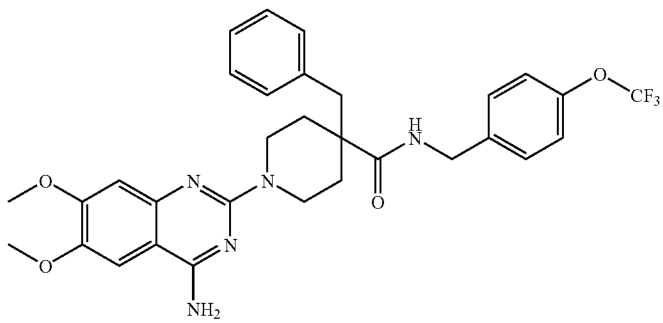 | 1-(4-Amino-6,7-dimethoxy-quinazolin-2-yl)-4-benzyl-piperidine-4-carboxylic acid 4-trifluoromethoxy-benzylamide | 1-(4-Amino-6,7-dimethoxy-quinazolin-2-yl)-4-benzyl-piperidine-4-carboxylic acid and 4-trifluoromethoxy-benzylamine (commercially available) | 596.4 |
| 27 | 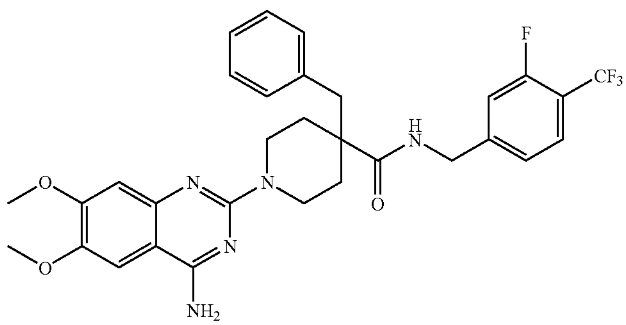 | 1-(4-Amino-6,7-dimethoxy-quinazolin-2-yl)-4-benzyl-piperidine-4-carboxylic acid 3-fluoro-4-trifluoromethyl-benzylamide | 1-(4-Amino-6,7-dimethoxy-quinazolin-2-yl)-4-benzyl-piperidine-4-carboxylic acid and 3-fluoro-4-trifluoromethyl-benzylamine (commercially available) | 598.3 |
| 28 | 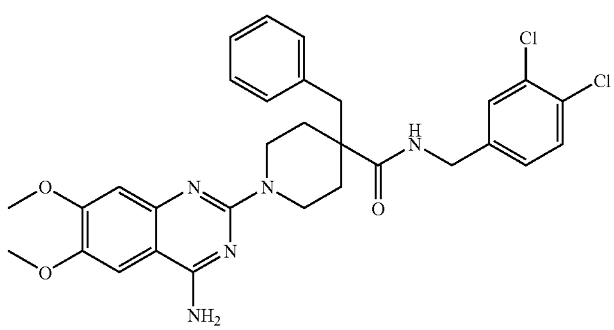 | 1-(4-Amino-6,7-dimethoxy-quinazolin-2-yl)-4-benzyl-piperidine-4-carboxylic acid 3,4-dichloro-benzylamide | 1-(4-Amino-6,7-dimethoxy-quinazolin-2-yl)-4-benzyl-piperidine-4-carboxylic acid and 3,4-dichloro-benzylamine (commercially available) | 580.3 |
| 29 | 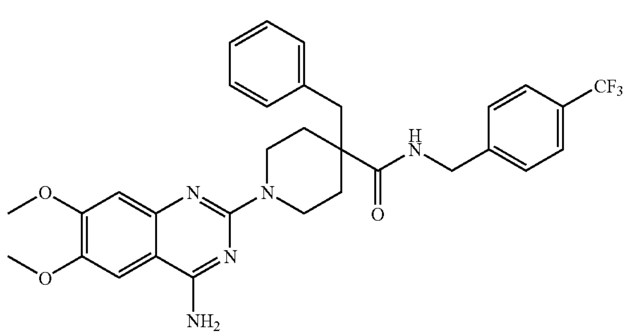 | 1-(4-Amino-6,7-dimethoxy-quinazolin-2-yl)-4-benzyl-piperidine-4-carboxylic acid 4-trifluoromethyl-benzylamide | 1-(4-Amino-6,7-dimethoxy-quinazolin-2-yl)-4-benzyl-piperidine-4-carboxylic acid and 4-trifluoromethyl-benzylamine (commercially available) | 580.4 |

TABLE 2-continued

| No | Structure | Systematic name | Starting materials | MW MH+ found |
|---|---|---|---|---|
| 30 | 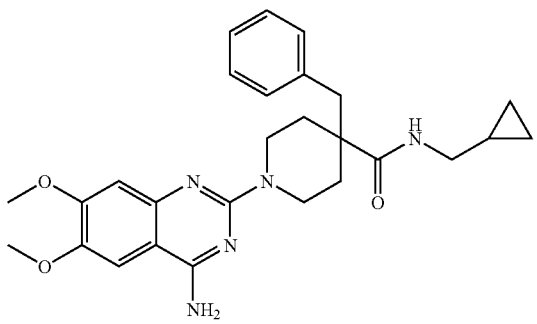 | 1-(4-Amino-6,7-dimethoxy-quinazolin-2-yl)-4-benzyl-piperidine-4-carboxylic acid cyclopropylmethyl-amide | 1-(4-Amino-6,7-dimethoxy-quinazolin-2-yl)-4-benzyl-piperidine-4-carboxylic acid and cyclopropylmethyl-amine (commercially available) | 476.3 |
| 31 | 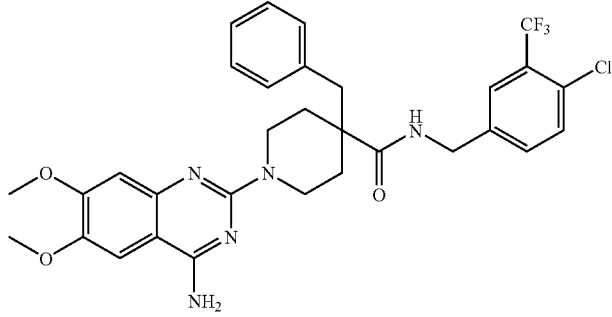 | 1-(4-Amino-6,7-dimethoxy-quinazolin-2-yl)-4-benzyl-piperidine-4-carboxylic acid 4-chloro-3-trifluoromethyl-benzylamide | 1-(4-Amino-6,7-dimethoxy-quinazolin-2-yl)-4-benzyl-piperidine-4-carboxylic acid and 4-chloro-3-trifluoromethyl-benzylamine (commercially available) | 614.2 |
| 32 | 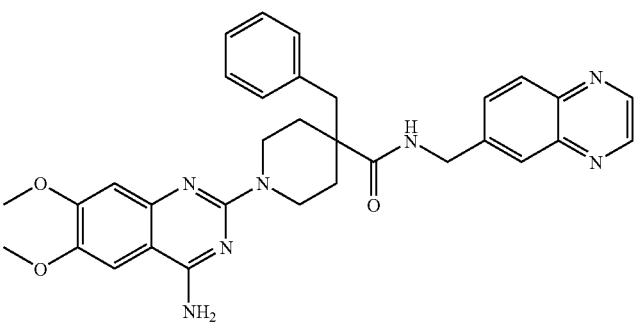 | 1-(4-Amino-6,7-dimethoxy-quinazolin-2-yl)-4-benzyl-piperidine-4-carboxylic acid (quinoxalin-6-ylmethyl)-amide | 1-(4-Amino-6,7-dimethoxy-quinazolin-2-yl)-4-benzyl-piperidine-4-carboxylic acid and (quinoxalin-6-ylmethyl)-amine (commercially available) | 564.4 |
| 33 | 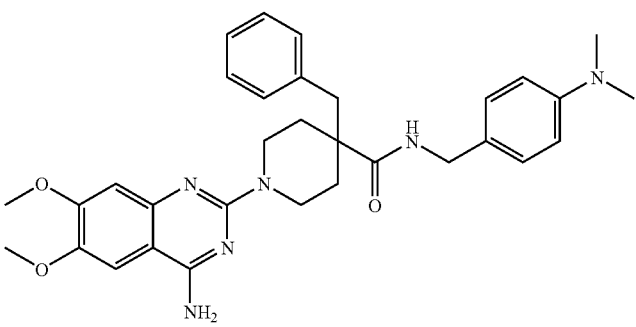 | 1-(4-Amino-6,7-dimethoxy-quinazolin-2-yl)-4-benzyl-piperidine-4-carboxylic acid 4-dimethylamino-benzylamide | 1-(4-Amino-6,7-dimethoxy-quinazolin-2-yl)-4-benzyl-piperidine-4-carboxylic acid and 4-dimethylamino-benzylamine (commercially available) | 555.3 |

TABLE 2-continued

| No | Structure | Systematic name | Starting materials | MW MH+ found |
|---|---|---|---|---|
| 34 | 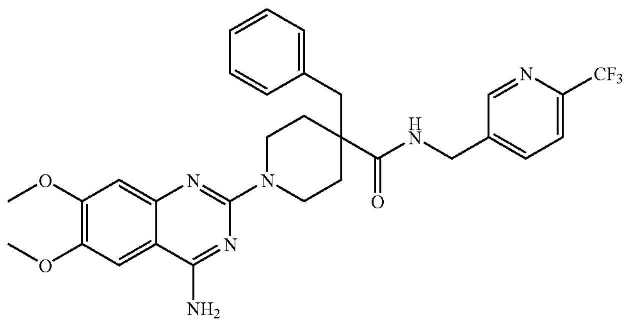 | 1-(4-Amino-6,7-dimethoxy-quinazolin-2-yl)-4-benzyl-piperidine-4-carboxylic acid (6-trilfuoromethyl-pyridin-3-ylmethyl)-amide | 1-(4-Amino-6,7-dimethoxy-quinazolin-2-yl)-4-benzyl-piperidine-4-carboxylic acid and (6-trifluoromethyl-pyridin-3-ylmethyl)-amine (commercially available) | 581.3 |
| 35 | 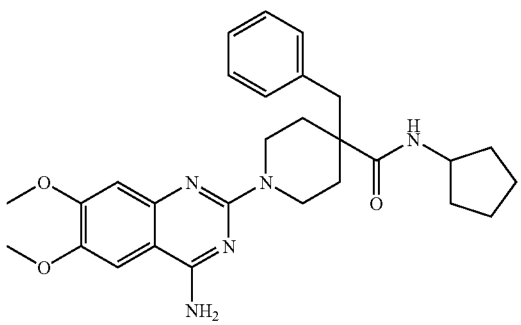 | 1-(4-Amino-6,7-dimethoxy-quinazolin-2-yl)-4-benzyl-piperidine-4-carboxylic acid cyclopentylamide | 1-(4-Amino-6,7-dimethoxy-quinazolin-2-yl)-4-benzyl-piperidine-4-carboxylic acid and cyclopentylamine (commercially available) | 490.4 |
| 36 | 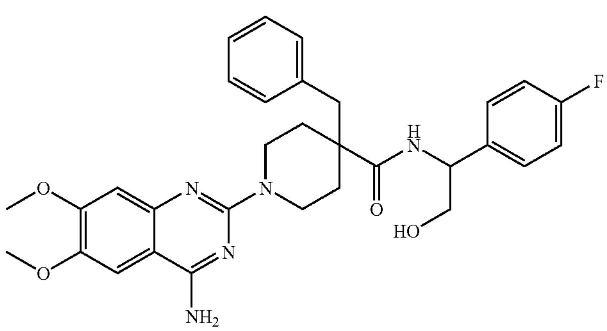 | 1-(4-Amino-6,7-dimethoxy-quinazolin-2-yl)-4-benzyl-piperidine-4-carboxylic acid [(R)-1-(4-fluoro-phenyl)-2-hydroxy-ethyl]-amide | 1-(4-Amino-6,7-dimethoxy-quinazolin-2-yl)-4-benzyl-piperidine-4-carboxylic acid and [(R)-1-(4-fluoro-phenyl)-2-hydroxy-ethyl]-amine (commercially available) | 560.3 |
| 37 | 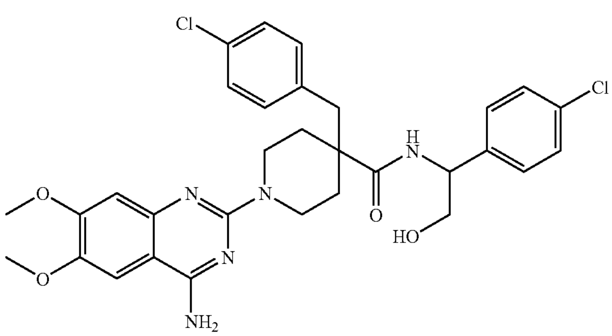 | 1-(4-Amino-6,7-dimethoxy-quinazolin-2-yl)-4-benzyl-piperidine-4-carboxylic acid [(R)-1-(4-chloro-phenyl)-2-hydroxy-ethyl]-amide | 1-(4-Amino-6,7-dimethoxy-quinazolin-2-yl)-4-benzyl-piperidine-4-carboxylic acid and [(R)-1-(4-chloro-phenyl)-2-hydroxy-ethyl]-amine (commercially available) | 576.4 |

TABLE 2-continued

| No | Structure | Systematic name | Starting materials | MW MH+ found |
|---|---|---|---|---|
| 38 | 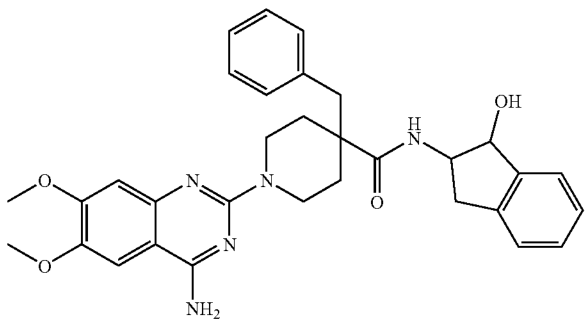 | 1-(4-Amino-6,7-dimethoxy-quinazolin-2-yl)-4-benzyl-piperidine-4-carboxylic acid (1-hydroxy-indan-2-yl)-amide | 1-(4-Amino-6,7-dimethoxy-quinazolin-2-yl)-4-benzyl-piperidine-4-carboxylic acid and (1-hydroxy-indan-2-yl)-amine (commercially available) | 554.3 |
| 39 | 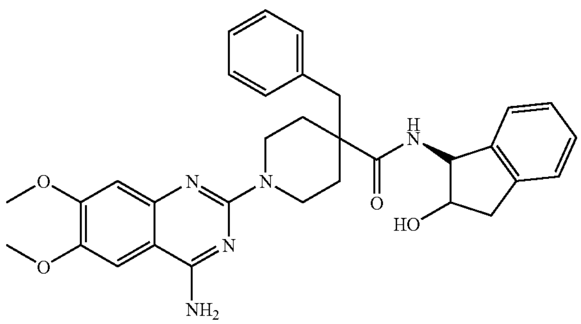 | 1-(4-Amino-6,7-dimethoxy-quinazolin-2-yl)-4-benzyl-piperidine-4-carboxylic acid ((1S,2S)-2-hydroxy-indan-1-yl)-amide | 1-(4-Amino-6,7-dimethoxy-quinazolin-2-yl)-4-benzyl-piperidine-4-carboxylic acid and ((1S,2S)-2-hydroxy-indan-1-yl)-amine (commercially available) | 554.3 |
| 40 | 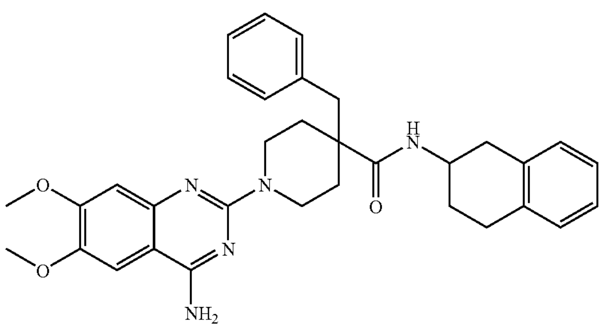 | 1-(4-Amino-6,7-dimethoxy-quinazolin-2-yl)-4-benzyl-piperidine-4-carboxylic acid (1,2,3,4-tetrahydro-naphthalen-2-yl)-amide | 1-(4-Amino-6,7-dimethoxy-quinazolin-2-yl)-4-benzyl-piperidine-4-carboxylic acid and (1,2,3,4-tetrahydro-naphthalen-2-yl)-amine (commercially available) | 552.4 |
| 41 | 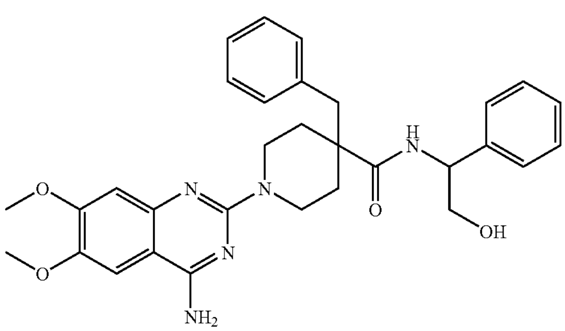 | 1-(4-Amino-6,7-dimethoxy-quinazolin-2-yl)-4-benzyl-piperidine-4-carboxylic acid (2-hydroxy-1-phenyl-ethyl)-amide | 1-(4-Amino-6,7-dimethoxy-quinazolin-2-yl)-4-benzyl-piperidine-4-carboxylic acid and (2-hydroxy-1-phenyl-ethyl)-amine (commercially available) | 542.3 |

TABLE 2-continued

| No | Structure | Systematic name | Starting materials | MW MH+ found |
|---|---|---|---|---|
| 42 | 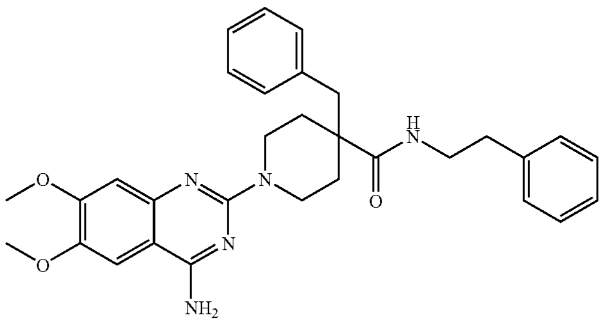 | 1-(4-Amino-6,7-dimethoxy-quinazolin-2-yl)-4-benzyl-piperidine-4-carboxylic acid phenethyl-amide | 1-(4-Amino-6,7-dimethoxy-quinazolin-2-yl)-4-benzyl-piperidine-4-carboxylic acid and phenethyl-amine (commercially available) | 526.4 |
| 43 | 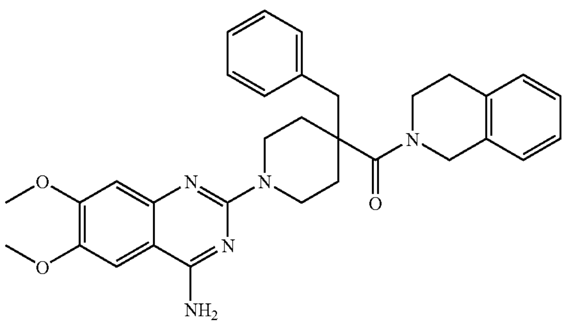 | [1-(4-Amino-6,7-dimethoxy-quinazolin-2-yl)-4-benzyl-piperidin-4-yl]-(3,4-dihydro-1H-isoquinolin-2-yl)-methanone | 1-(4-Amino-6,7-dimethoxy-quinazolin-2-yl)-4-benzyl-piperidine-4-carboxylic acid and tetrahydrosioquinoline (commercially available) | 538.4 |
| 44 | 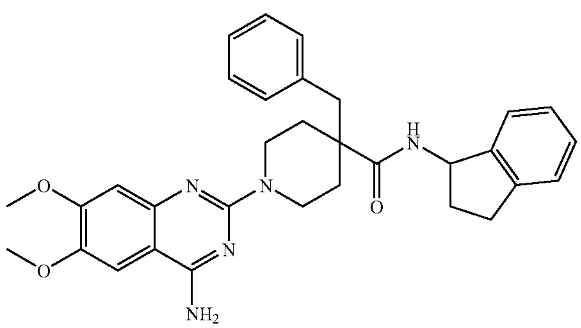 | 1-(4-Amino-6,7-dimethoxy-quinazolin-2-yl)-4-benzyl-piperidine-4-carboxylic acid indan-1-ylamide | 1-(4-Amino-6,7-dimethoxy-quinazolin-2-yl)-4-benzyl-piperidine-4-carboxylic acid and indan-1-ylamine (commercially available) | 538.4 |
| 45 | 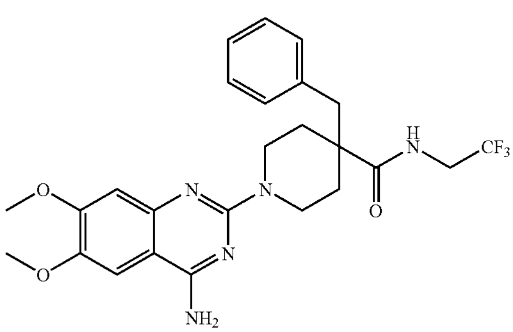 | 1-(4-Amino-6,7-dimethoxy-quinazolin-2-yl)-4-benzyl-piperidine-4-carboxylic acid (2,2,2-trifluoro-ethyl)-amide | 1-(4-Amino-6,7-dimethoxy-quinazolin-2-yl)-4-benzyl-piperidine-4-carboxylic acid and (2,2,2-trifluoro-ethyl)-amine (commercially available) | 504.2 |

TABLE 2-continued

| No | Structure | Systematic name | Starting materials | MW MH+ found |
|---|---|---|---|---|
| 46 | 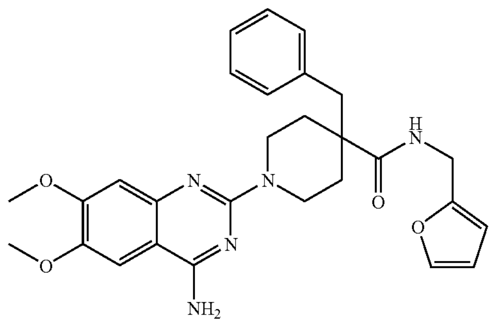 | 1-(4-Amino-6,7-dimethoxy-quinazolin-2-yl)-4-benzyl-piperidine-4-carboxylic acid (furan-2-ylmethyl)-amide | 1-(4-Amino-6,7-dimethoxy-quinazolin-2-yl)-4-benzyl-piperidine-4-carboxylic acid and (furan-2-ylmethyl)-amine (commercially available) | 502.3 |
| 47 | 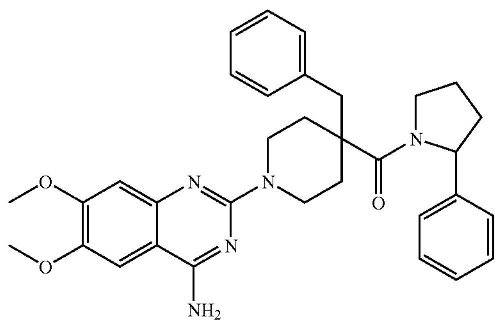 | [1-(4-Amino-6,7-dimethoxy-quinazolin-2-yl)-4-benzyl-piperidin-4-yl]-(2-phenyl-pyrrolidin-1-yl)-methanone | 1-(4-Amino-6,7-dimethoxy-quinazolin-2-yl)-4-benzyl-piperidine-4-carboxylic acid and 2-Phenyl-pyrrolidine (commercially available) | 552.4 |
| 48 | 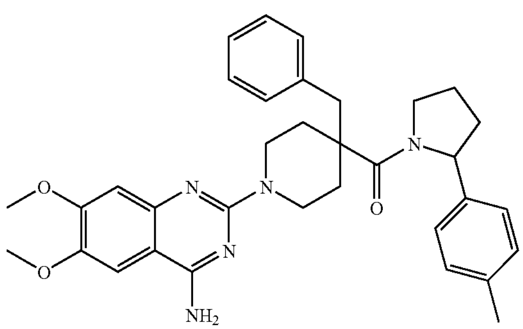 | [1-(4-Amino-6,7-dimethoxy-quinazolin-2-yl)-4-benzyl-piperidin-4-yl]-[2-(4-fluoro-phenyl)-pyrrolidin-1-yl]-methanone | 1-(4-Amino-6,7-dimethoxy-quinazolin-2-yl)-4-benzyl-piperidine-4-carboxylic acid and 2-(4-Fluoro-phenyl)-pyrrolidine (commercially available) | 570.4 |
| 49 | 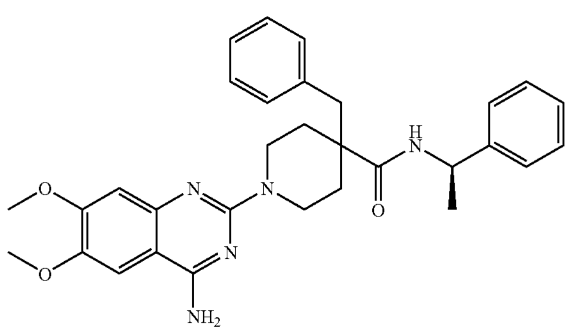 | 1-(4-Amino-6,7-dimethoxy-quinazolin-2-yl)-4-benzyl-piperidine-4-carboxylic acid ((R)-1-phenyl-ethyl)-amide | 1-(4-Amino-6,7-dimethoxy-quinazolin-2-yl)-4-benzyl-piperidine-4-carboxylic acid and ((R)-1-phenyl-ethyl)-amine (commercially available) | 526.4 |

TABLE 2-continued

| No | Structure | Systematic name | Starting materials | MW MH+ found |
|---|---|---|---|---|
| 50 | 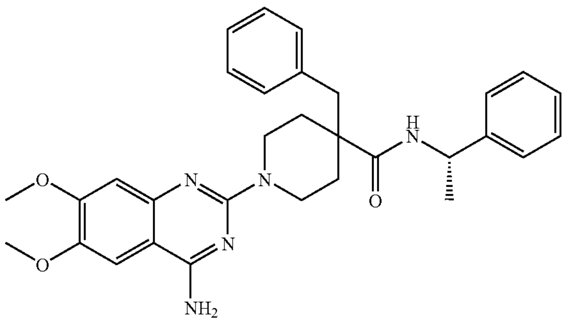 | 1-(4-Amino-6,7-dimethoxy-quinazolin-2-yl)-4-benzyl-piperidine-4-carboxylic acid ((S)-1-phenyl-ethyl)-amide | 1-(4-Amino-6,7-dimethoxy-quinazolin-2-yl)-4-benzyl-piperidine-4-carboxylic acid and ((S)-1-phenyl-ethyl)-amine (commercially available) | 526.4 |
| 51 | 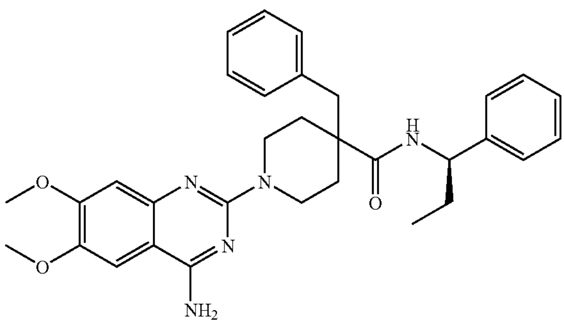 | 1-(4-Amino-6,7-dimethoxy-quinazolin-2-yl)-4-benzyl-piperidine-4-carboxylic acid ((R)-1-phenyl-propyl)-amide | 1-(4-Amino-6,7-dimethoxy-quinazolin-2-yl)-4-benzyl-piperidine-4-carboxylic acid and ((R)-1-phenyl-propyl)-amine (commercially available) | 540.4 |
| 52 | 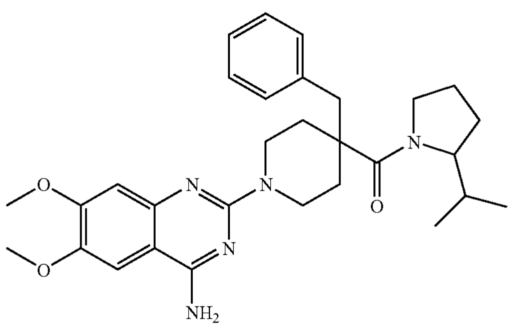 | [1-(4-Amino-6,7-dimethoxy-quinazolin-2-yl)-4-benzyl-piperidin-4-yl]-(2-isopropyl-pyrrolidin-1-yl)-methanone | 1-(4-Amino-6,7-dimethoxy-quinazolin-2-yl)-4-benzyl-piperidine-4-carboxylic acid and 2-Isopropyl-pyrroldiine (commercially available) | 518.3 |
| 53 | 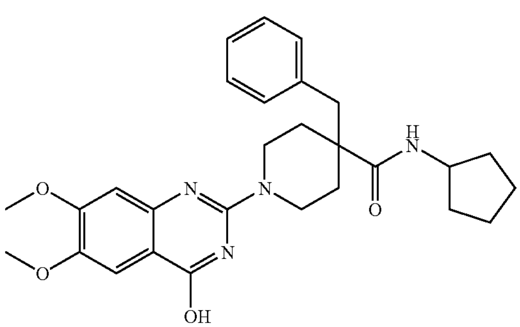 | 4-Benzyl-1-(4-hydroxy-6,7-dimethoxy-quinazolin-2-yl)-piperidine-4-carboxylic acid cyclopentylamide | 4-Benzyl-1-(4-hydroxy-6,7-dimethoxy-quinazolin-2-yl)-piperidine-4-carboxylic acid (Intermediate 6) and cyclopentylamine (commercially available) | 491.3 |

TABLE 2-continued

| No | Structure | Systematic name | Starting materials | MW MH+ found |
|---|---|---|---|---|
| 54 | 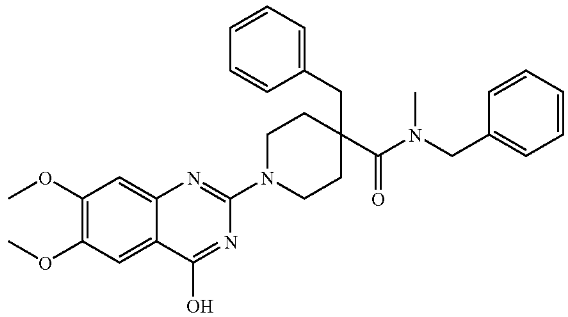 | 4-Benzyl-1-(4-hydroxy-6,7-dimethoxy-quinazolin-2-yl)-piperidine-4-carboxylic acid benzyl-methyl-amide | 4-Benzyl-1-(4-hydroxy-6,7-dimethoxy-quinazolin-2-yl)-piperidine-4-carboxylic acid (Intermediate 6) and benzyl-methyl-amine (commercially available) | 527.4 |
| 55 | 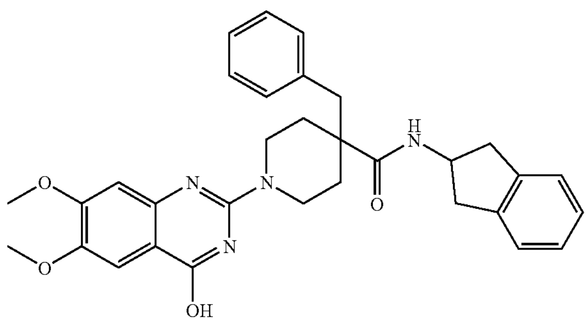 | 4-Benzyl-1-(4-hydroxy-6,7-dimethoxy-quinazolin-2-yl)-piperidine-4-carboxylic acid indan-2-ylamide | 4-Benzyl-1-(4-hydroxy-6,7-dimethoxy-quinazolin-2-yl)-piperidine-4-carboxylic acid (Intermediate 6) and indan-2-ylamine (commercially available) | 539.4 |
| 56 | 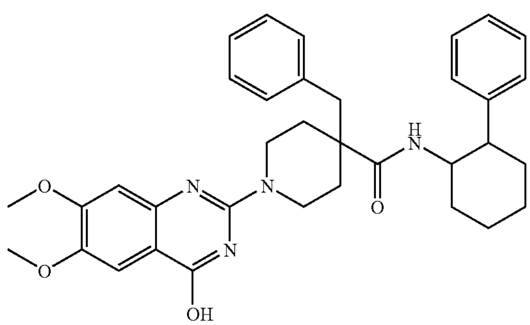 | 4-Benzyl-1-(4-hydroxy-6,7-dimethoxy-quinazolin-2-yl)-piperidine-4-carboxylic acid (2-phenyl-cyclohexyl)-amide | 4-Benzyl-1-(4-hydroxy-6,7-dimethoxy-quinazolin-2-yl)-piperidine-4-carboxylic acid (Intermediate 6) and (2-phenyl-cyclohexyl)-amine (commercially available) | 581.3 |
| 57 | 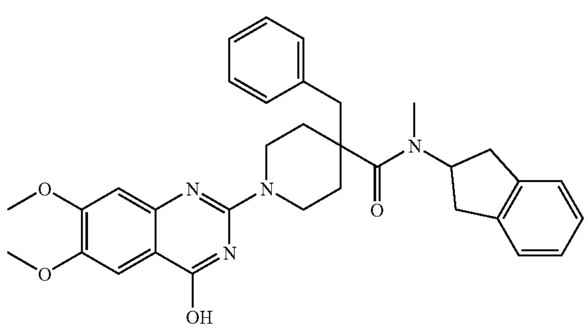 | 4-Benzyl-1-(4-hydroxy-6,7-dimethoxy-quinazolin-2-yl)-piperidine-4-carboxylic acid indan-2-yl-methyl-amide | 4-Benzyl-1-(4-hydroxy-6,7-dimethoxy-quinazolin-2-yl)-piperidine-4-carboxylic acid (Intermediate 6) and indan-2-yl-methyl-amine (commercially available) | 553.4 |

TABLE 2-continued

| No | Structure | Systematic name | Starting materials | MW MH+ found |
|---|---|---|---|---|
| 58 | 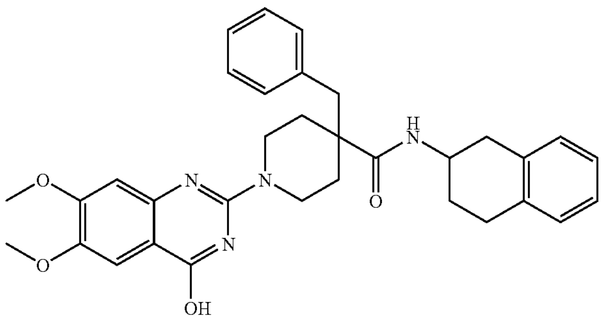 | 4-Benzyl-1-(4-hydroxy-6,7-dimethoxy-quinazolin-2-yl)-piperidine-4-carboxylic acid (1,2,3,4-tetrahydro-naphthalen-2-yl)-amide | 4-Benzyl-1-(4-hydroxy-6,7-dimethoxy-quinazolin-2-yl)-piperidine-4-carboxylic acid (Intermediate 6) and (1,2,3,4-tetrahydro-naphthalen-2-yl)-amine (commercially available) | 553.4 |
| 59 | 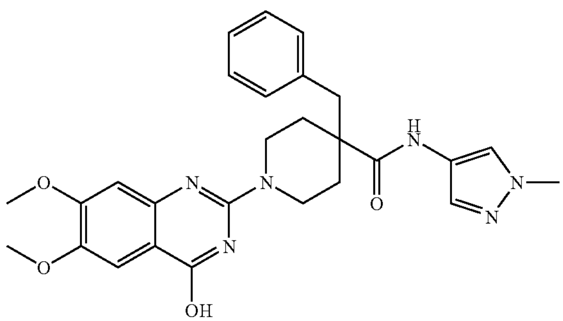 | 4-Benzyl-1-(4-hydroxy-6,7-dimethoxy-quinazolin-2-yl)-piperidine-4-carboxylic acid (1-methyl-1H-pyrazol-4-yl)-amide | 4-Benzyl-1-(4-hydroxy-6,7-dimethoxy-quinazolin-2-yl)-piperidine-4-carboxylic acid (Intermediate 6) and (1-methyl-1H-pyrazol-4-yl)-amine (commercially available) | 503.2 |
| 60 | 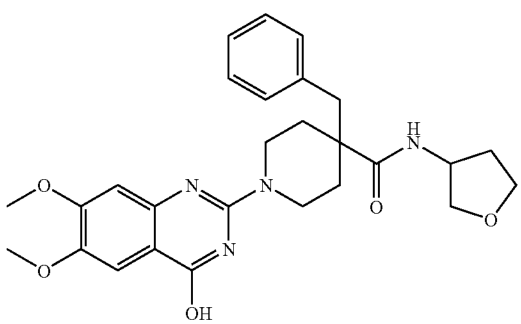 | 4-Benzyl-1-(4-hydroxy-6,7-dimethoxy-quinazolin-2-yl)-piperidine-4-carboxylic acid (tetrahydro-furan-3-yl)-amide | 4-Benzyl-1-(4-hydroxy-6,7-dimethoxy-quinazolin-2-yl)-piperidine-4-carboxylic acid (Intermediate 6) and (tetrahydro-furan-3-yl)-amine (commercially available) | 493.3 |
| 61 | 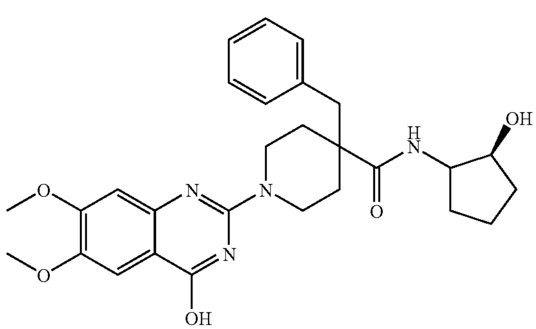 | 4-Benzyl-1-(4-hydroxy-6,7-dimethoxy-quinazolin-2-yl)-piperidine-4-carboxylic acid ((1S,2S)-2-hydroxy-cyclopentyl)-amide | 4-Benzyl-1-(4-hydroxy-6,7-dimethoxy-quinazolin-2-yl)-piperidine-4-carboxylic acid (Intermediate 6) and ((1S,2S)-2-hydroxy-cyclopentyl)-amine (commercially available) | 507.3 |

TABLE 2-continued

| No | Structure | Systematic name | Starting materials | MW MH+ found |
|---|---|---|---|---|
| 62 | 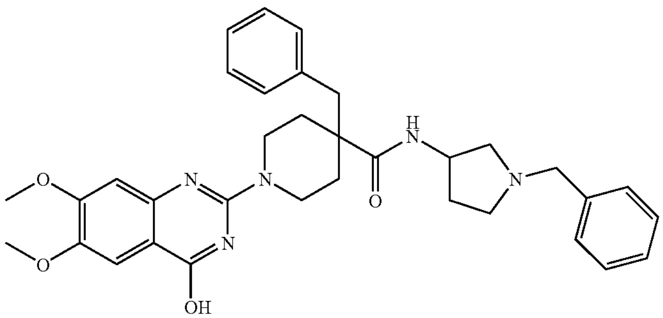 | 4-Benzyl-1-(4-hydroxy-6,7-dimethoxy-quinazolin-2-yl)-piperidine-4-carboxylic acid (1-benzyl-pyrrolidin-3-yl)-amide | 4-Benzyl-1-(4-hydroxy-6,7-dimethoxy-quinazolin-2-yl)-piperidine-4-carboxylic acid (Intermediate 6) and (1-benzyl-pyrroldiin-3-yl)-amine (commercially available) | 582.3 |
| 63 | 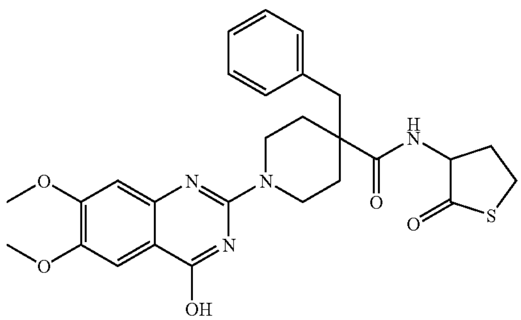 | 4-Benzyl-1-(4-hydroxy-6,7-dimethoxy-quinazolin-2-yl)-piperidine-4-carboxylic acid (2-oxo-tetrahydro-thiophen-3-yl)-amide | 4-Benzyl-1-(4-hydroxy-6,7-dimethoxy-quinazolin-2-yl)-piperidine-4-carboxylic acid (Intermediate 6) and (2-oxo-tetrahydro-thiophen-3-yl)-amine (commercially available) | 523.4 |
| 64 | 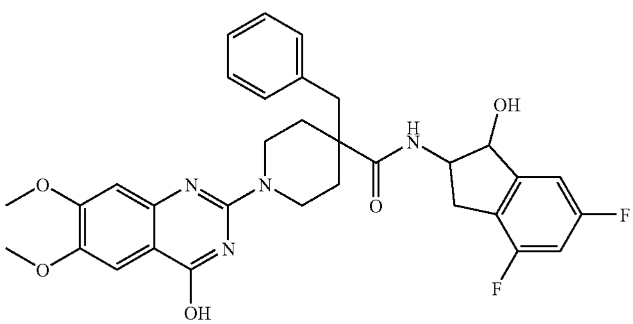 | 4-Benzyl-1-(4-hydroxy-6,7-dimethoxy-quinazolin-2-yl)-piperidine-4-carboxylic acid (4,6-difluoro-1-hydroxy-indan-2-yl)-amide | 4-Benzyl-1-(4-hydroxy-6,7-dimethoxy-quinazolin-2-yl)-piperidine-4-carboxylic acid (Intermediate 6) and (4,6-difluoro-1-hydroxy-indan-2-yl)-amine (commercially available) | 591.4 |
| 65 | 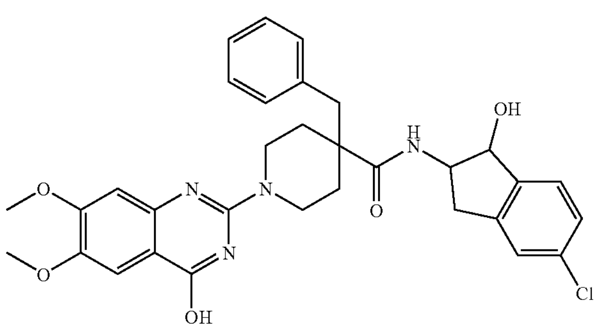 | 4-Benzyl-1-(4-hydroxy-6,7-dimethoxy-quinazolin-2-yl)-piperidine-4-carboxylic acid (5-chloro-1-hydroxy-indan-2-yl)-amide | 4-Benzyl-1-(4-hydroxy-6,7-dimethoxy-quinazolin-2-yl)-piperidine-4-carboxylic acid (Intermediate 6) and (5-chloro-1-hydroxy-indan-2-yl)-amine (commercially available) | 591.4 |

TABLE 2-continued

| No | Structure | Systematic name | Starting materials | MW MH+ found |
|---|---|---|---|---|
| 66 | 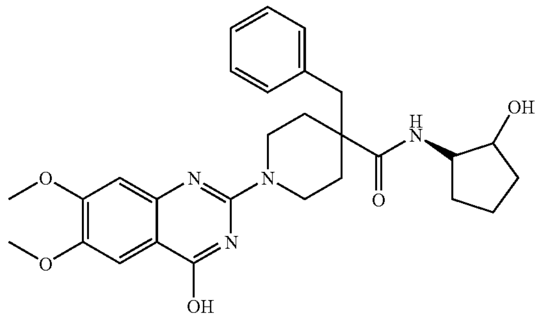 | 4-Benzyl-1-(4-hydroxy-6,7-dimethoxy-quinazolin-2-yl)-piperidine-4-carboxylic acid ((1R,2S)-2-hydroxy-cyclopentyl)-amide | 4-Benzyl-1-(4-hydroxy-6,7-dimethoxy-quinazolin-2-yl)-piperidine-4-carboxylic acid (Intermediate 6) and ((1R,2S)-2-hydroxy-cyclopentyl)-amine (commercially available) | 507.3 |
| 67 | 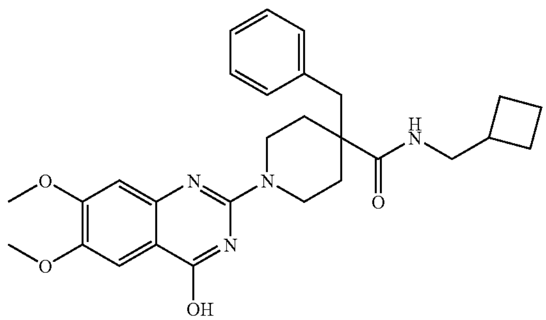 | 4-Benzyl-1-(4-hydroxy-6,7-dimethoxy-quinazolin-2-yl)-piperidine-4-carboxylic acid cyclobutylmethyl-amide | 4-Benzyl-1-(4-hydroxy-6,7-dimethoxy-quinazolin-2-yl)-piperidine-4-carboxylic acid (Intermediate 6) and cyclobutylmethyl-amine (commercially available) | 491.4 |
| 68 | 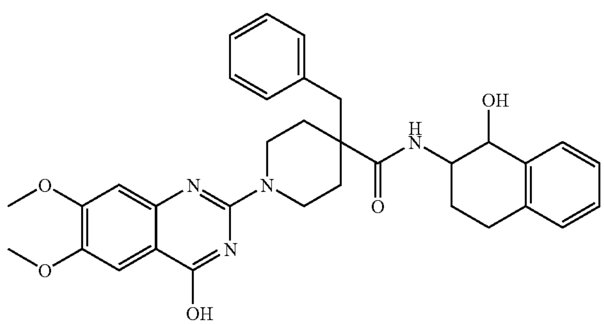 | 4-Benzyl-1-(4-hydroxy-6,7-dimethoxy-quinazolin-2-yl)-piperidine-4-carboxylic acid (1-hydroxy-1,2,3,4-tetrahydro-naphthalen-2-yl)-amide | 4-Benzyl-1-(4-hydroxy-6,7-dimethoxy-quinazolin-2-yl)-piperidine-4-carboxylic acid (Intermediate 6) and (1-hydroxy-1,2,3,4-tetrahydro-naphthalen-2-yl)-amine (commercially available) | 569.5 |
| 69 | 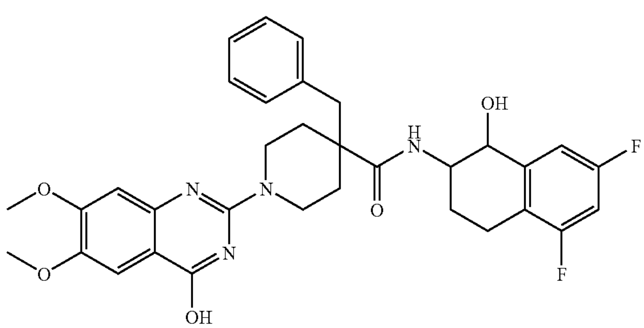 | 4-Benzyl-1-(4-hydroxy-6,7-dimethoxy-quinazolin-2-yl)-piperidine-4-carboxylic acid (5,7-difluoro-1-hydroxy-1,2,3,4-tetrahydro-naphthalen-2-yl)-amide | 4-Benzyl-1-(4-hydroxy-6,7-dimethoxy-quinazolin-2-yl)-piperidine-4-carboxylic acid (Intermediate 6) and (5,7-difluoro-1-hydroxy-1,2,3,4-tetrahydro-naphthlen-2-yl)-amine (commercially available) | 605.5 |

TABLE 2-continued

| No | Structure | Systematic name | Starting materials | MW MH+ found |
|---|---|---|---|---|
| 70 | 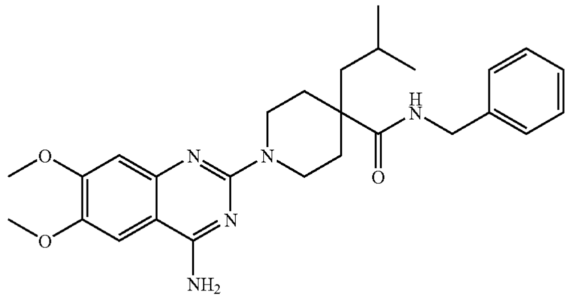 | 1-(4-Amino-6,7-dimethoxy-quinazolin-2-yl)-4-isobutyl-piperidine-4-carboyxlic acid benzylamide | 1-(4-Amino-6,7-dimethoxy-quinazolin-2-yl)-4-isobutyl-piperidine-4-carboxylic acid (intermediate 7) and benzylamine (commercially available) | 478.2 |
| 71 | 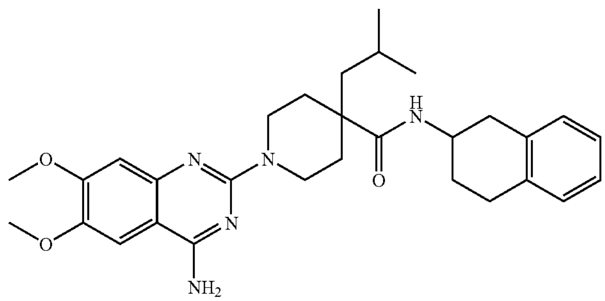 | 1-(4-Amino-6,7-dimethoxy-quinazolin-2-yl)-4-isobutyl-piperidine-4-carboxylic acid (1,2,3,4-tetrahydro-naphthalen-2-yl)-amide | 1-(4-Amino-6,7-dimethoxy-quinazolin-2-yl)-4-isobutyl-piperidine-4-carboxylic acid (intermediate 7) and (1,2,3,4-tetrahydro-naphthlane-2-yl)-amine (commercially available) | 518.4 |
| 72 | 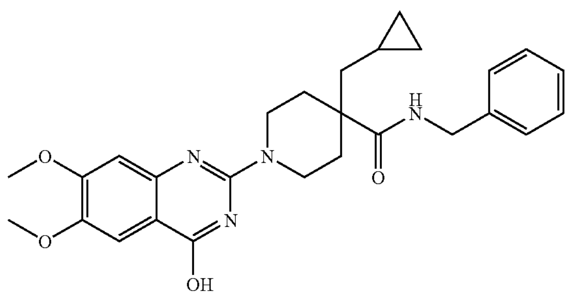 | 4-Cyclopropylmethyl-1-(4-hydroxy-6,7-dimethoxy-quinazolin-2-yl)-piperidine-4-carboxylic acid benzylamide | 4-Cyclopropylmethyl-1-(4-hydroxy-6,7-dimethoxy-quinazolin-2-yl)-piperidine-4-carboxylic acid (Intermediate 8) and benzylamine (commercially available) | 206.2/ 477.3 |
| 73 | 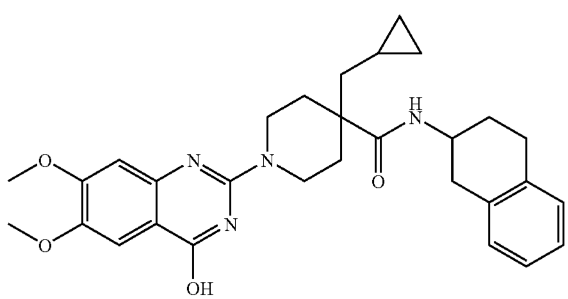 | 4-Cyclopropylmethyl-1-(4-hydroxy-6,7-dimethoxy-quinazolin-2-yl)-piperidine-4-carboxylic acid (1,2,3,4-tetrahydro-naphthalen-2-yl)-amide | 4-Cyclopropylmethyl-1-(4-hydroxy-6,7-dimethoxy-quinazolin-2-yl)-piperidine-4-carboxylic acid (Intermediate 8) and (1,2,3,4-tetrahydro-naphthalen-2-yl)-amine (commercially available) | 206.2/ 517.3 |
| 74 | 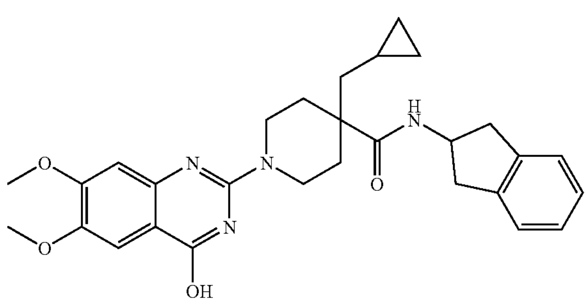 | 4-Cylcopropylmethyl-1-(4-hydroxy-6,7-dimethoxy-quinazolin-2-yl)-piperidine-4-carboxylic acid indan-2-ylamide | 4-Cylcopropylmethyl-1-(4-hydroxy-6,7-dimethoxy-quinazolin-2-yl)-piperidine-4-carboxylic acid (Intermediate 8) and indan-2-ylamine (commercially available) | 246.3/ 503.3 |

TABLE 2-continued

| No | Structure | Systematic name | Starting materials | MW MH+ found |
|---|---|---|---|---|
| 75 | 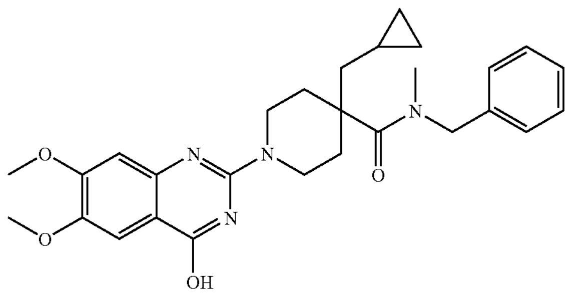 | 4-Cylcopropylmethyl-1-(4-hydroxy-6,7-dimethoxy-quinazolin-2-yl)-piperidine-4-carobxylic acid benzyl-methyl-amide | 4-Cyclopropylmethyl-1-(4-hydroxy-6,7-dimethoxy-quinazolin-2-yl)-piperidine-4-carboxylic acid (Intermediate 8) and benzyl-methyl-amine (commercially available) | 232.2/ 491.3 |
| 76 | 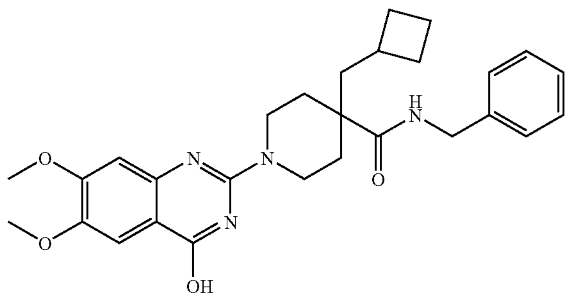 | 4-Cyclobutylmethyl-1-(4-hydroxy-6,7-dimethoxy-quinazolin-2-yl)-piperidine-4-carboxylic acid benzylamide | 4-Cylcobutylmethyl-1-(4-hydroxy-6,7-dimethoxy-quinazolin-2-yl)-piperidine-4-carboxylic acid (Intermediate 9) and benzylamine (commercially available) | 220.3/ 491.3 |
| 77 | 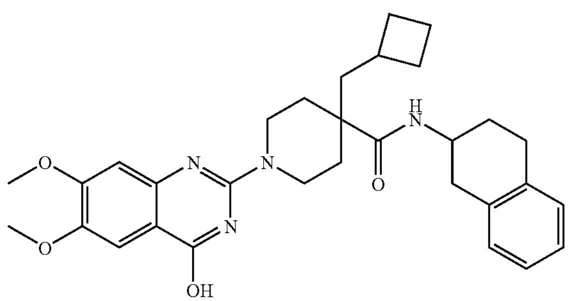 | 4-Cylcobutylmethyl-1-(4-hydroxy-6,7-dimethoxy-quinazolin-2-yl)-piperidine-4-carboxylic acid (1,2,3,4-tetrahydro-naphthalen-2-yl)-amide | 4-Cyclobutylmethyl-1-(4-hydroxy-6,7-dimethoxy-quinazolin-2-yl)-piperidine-4-carboxylic acid (Intermediate 9) and (1,2,3,4-tetrahydro-naphthalen-2-yl)-amine (commercially available) | 206.2/ 531.2 |
| 78 | 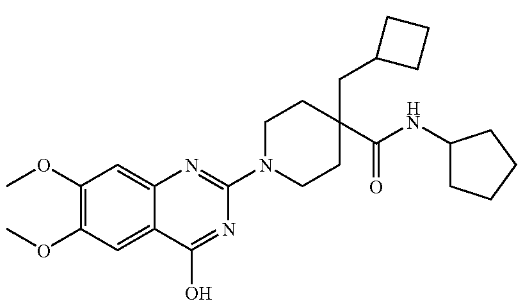 | 4-Cyclobutylmethyl-1-(4-hydroxy-6,7-dimethoxy-quinazolin-2-yl)-piperidine-4-carboxylic acid cyclopentylamide | 4-Cyclobutylmethyl-1-(4-hydroxy-6,7-dimethoxy-quinazolin-2-yl)-piperidine-4-carboxylic acid (Intermediate 9) and cyclopentylamine (commercially available) | 246.3/ 469.4 |
| 79 | 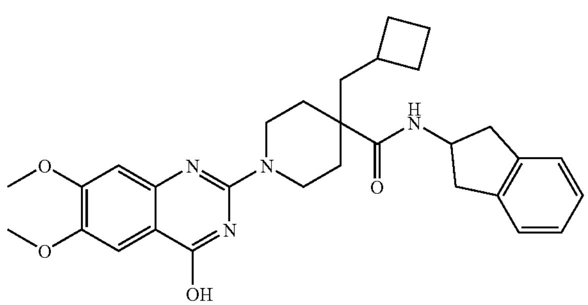 | 4-Cyclobutylmethyl-1-(4-hydroxy-6,7-dimethoxy-quinazolin-2-yl)-piperidine-4-carboxylic acid indan-2-ylamide | 4-Cyclobutylmethyl-1-(4-hydroxy-6,7-dimethoxy-quinazolin-2-yl)-piperidine-4-carboxylic acid (Intermediate 9) and indan-2-ylamine (commercially available) | 246.3/ 517.3 |

TABLE 2-continued

| No | Structure | Systematic name | Starting materials | MW MH+ found |
|---|---|---|---|---|
| 80 | 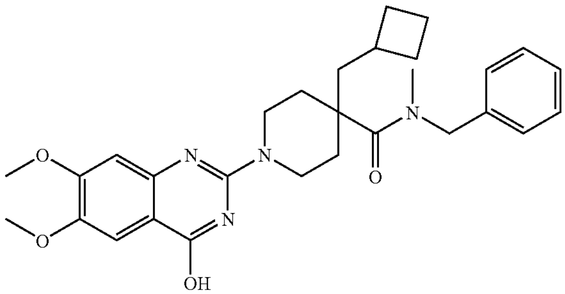 | 4-Cyclobutylmethyl-1-(4-hydroxy-6,7-dimethoxy-quinazolin-2-yl)-piperidine-4-carboxylic acid benzyl-methyl-amide | 4-Cyclobutylmethyl-1-(4-hydroxy-6,7-dimethoxy-quinazolin-2-yl)-piperidine-4-carboxylic acid (Intermediate 9) and benzyl-methyl-amine (commercially available) | 505.3 |

Example 81

4-Benzyl-1-(4-hydroxy-6-trifluoromethoxy-quinazolin-2-yl)-piperidine-4-carboxylic acid benzylamide

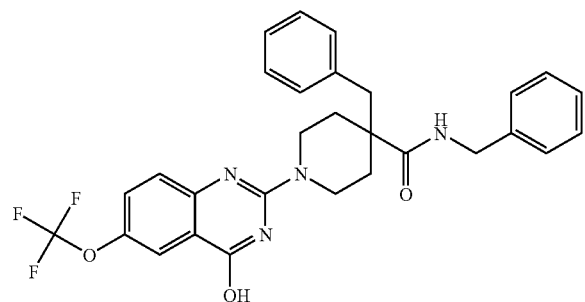

A mixture of 26.6 mg (0.15 mmol) 4-trifluoromethoxy-phenylamine (commercially available) and 21.6 mg (0.165 mmol) ethyl isocyanatoformate in 3 mL DCM was stirred at room temperature overnight. A mixture of 53 mg (0.172 mmol) 4-benzyl-piperidine-4-carboxylic acid benzylamide (commercially available), 45 mg (0.45 mmol) NEt$_3$ and 34 mg (0.18 mmol) EDCI in DCM was added and the solution was stirred at room temperature. The mixture was absorbed on isolute and purified by flash column chromatography on silica eluting with a gradient formed from DCM, methanol and ammonia (2N). The product containing fractions were evaporated to dryness and taken up in 2 mL DMF. 163.9 mg (1.5 mmol) trimethylchlorosilane was added and the mixture was heated to 85° C. overnight. The mixture was subjected to purification by preparative HPLC on reversed phase eluting with a gradient formed from acetonitrile, water and NEt$_3$. The product containing fractions were evaporated to yield the title compound as off-white solid. MS(m/e): 537.3 (M+H$^+$)

In analogy to the procedure described for the synthesis of 4-Benzyl-1-(4-hydroxy-6-trifluoromethoxy-quinazolin-2-yl)-piperidine-4-carboxylic acid benzylamide (example 81) further quinazoline derivatives have been synthesised from their respective starting materials as mentioned in table 3. Table 3 comprises example 82-100.

TABLE 3

| NO | structure | Systematic Name | starting materials | MW MH+ found |
|---|---|---|---|---|
| 81 | 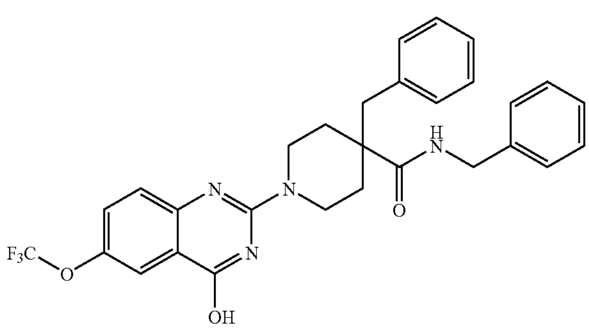 | 4-Benzyl-1-(4-hydroxy-6-trifluoromethoxy-quinazolin-2-yl)-piperidine-4-carboxylic acid benzylamide | 4-Trifluoromethoxy-phenylamine (commercially available) and 4-benzyl-piperidine-4-carboxylic acid benzylamide (commercially available) | 537.3 |

TABLE 3-continued

| NO | structure | Systematic Name | starting materials | MW MH+ found |
|---|---|---|---|---|
| 82 | 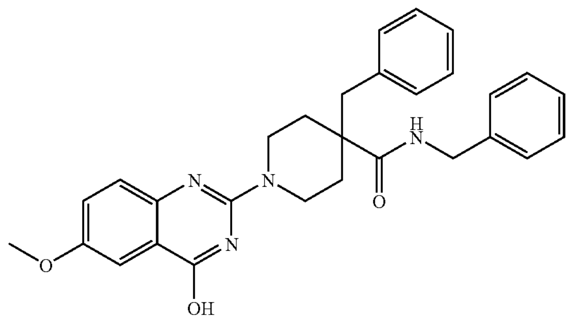 | 4-Benzyl-1-(4-hydroxy-6-methoxy-quinazolin-2-yl)-piperidine-4-carboxylic acid benzylamide | 4-Methoxy-phenylamine (commercially available) and 4-benzyl-piperidine-4-carboxylic acid benzylamide (commercially available) | 483.3 |
| 83 | 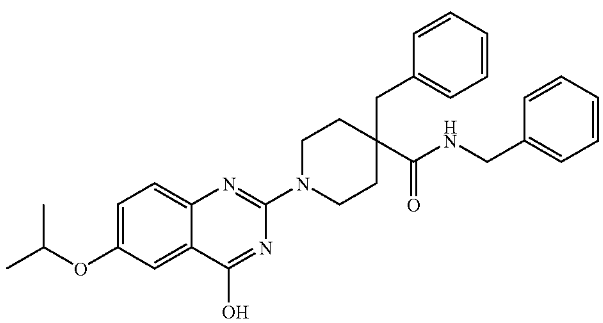 | 4-Benzyl-1-(4-hydroxy-6-isopropoxy-quinazolin-2-yl)-piperidine-4-carboxylic acid benzylamide | 4-Isopropoxy-phenylamine (commercially available) and 4-benzyl-piperidine-4-carboxylic acid benzylamide (commercially available) | 511.4 |
| 84 | 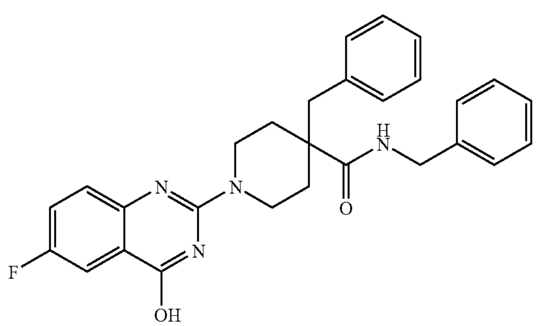 | 4-Benzyl-1-(6-fluoro-4-hydroxy-quinazolin-2-yl)-piperidine-4-carboxylic acid benzylamide | 4-Fluoro-phenylamine (commercially available) and 4-benzyl-piperidine-4-carboxylic acid benzylamide (commercially available) | 471.4 |
| 85 | 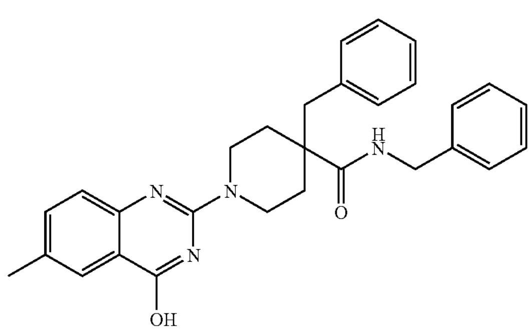 | 4-Benzyl-1-(4-hydroxy-6-methyl-quinazolin-2-yl)-piperidine-4-carboxylic acid benzylamide | p-Tolylamine (commercially available) and 4-benzyl-piperidine-4-carboxylic acid benzylamide (commercially available) | 467.3 |

TABLE 3-continued

| NO | structure | Systematic Name | starting materials | MW MH+ found |
|---|---|---|---|---|
| 86 | 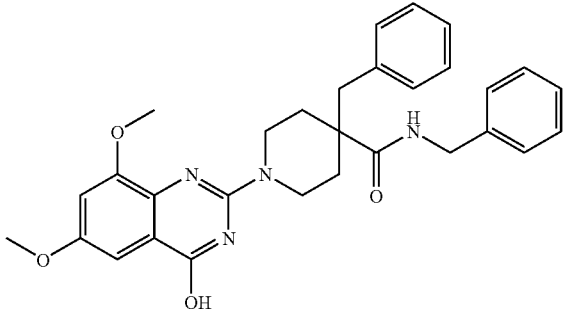 | 4-Benzyl-1-(4-hydroxy-6,8-dimethoxy-quinazolin-2-yl)-piperidine-4-carboxylic acid benzylamide | 2,4-Dimethoxy-phenylamine (commercially available) and 4-benzyl-piperidine-4-carboxylic acid benzylamide (commercially available) | 513.4 |
| 87 | 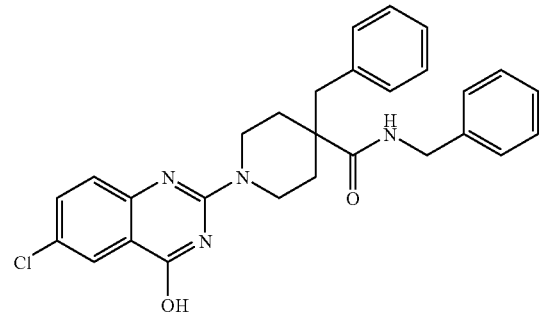 | 4-Benzyl-1-(6-chloro-4-hydroxy-quinazolin-2-yl)-piperidine-4-carboxylic acid benzylamide | 4-Chloro-phenylamine (commercially available) and 4-benzyl-piperidine-4-carboxylic acid benzylamide (commercially available) | 487.3 |
| 88 | 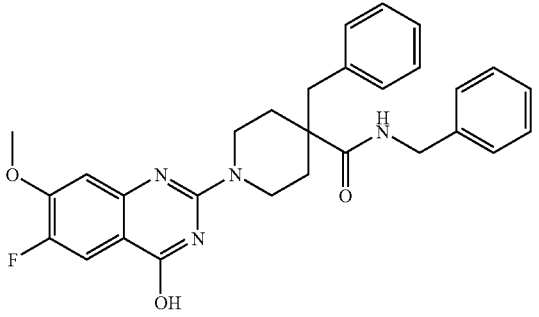 | 4-Benzyl-1-(6-fluoro-4-hydroxy-7-methoxy-quinazolin-2-yl)-piperidine-4-carboxylic acid benzylamide | 4-Fluoro-3-methoxy-phenylamine (commercially available) and 4-benzyl-piperidine-4-carboxylic acid benzylamide (commercially available) | 501.2 |
| 89 | 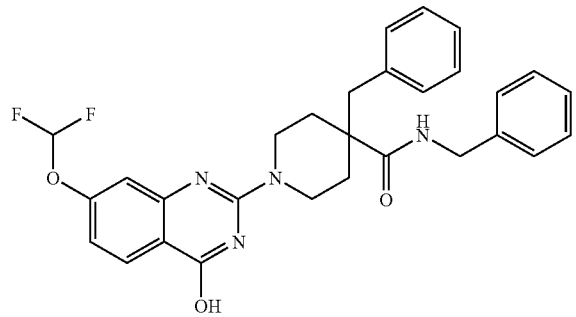 | 4-Benzyl-1-(7-difluoromethoxy-4-hydroxy-quinazolin-2-yl)-piperidine-4-carboxylic acid benzylamide | 3-Difluoromethoxy-phenylamine (commercially available) and 4-benzyl-piperidine-4-carboxylic acid benzylamide (commercially available) | 519.3 |

TABLE 3-continued

| NO | structure | Systematic Name | starting materials | MW MH+ found |
|---|---|---|---|---|
| 90 | 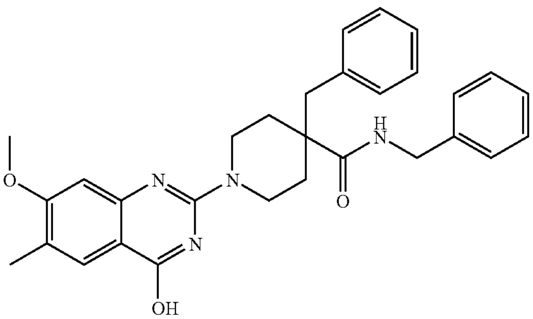 | 4-Benzyl-1-(4-hydroxy-7-methoxy-6-methyl-quinazolin-2-yl)-piperidine-4-carboxylic acid benzylamide | 3-Methoxy-4-methyl-phenylamine (commercially available) and 4-benzyl-piperidine-4-carboxylic acid benzylamide (commercially available) | 497.3 |
| 91 | 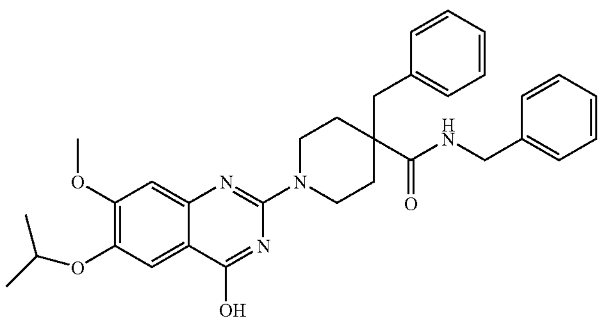 | 4-Benzyl-1-(4-hydroxy-6-isopropoxy-7-methoxy-quinazolin-2-yl)-piperidine-4-carboxylic acid benzylamide | 4-Isopropoxy-3-methoxy-phenylamine (commercially available) and 4-benzyl-piperidine-4-carboxylic acid benzylamide (commercially available) | 541.3 |
| 92 | 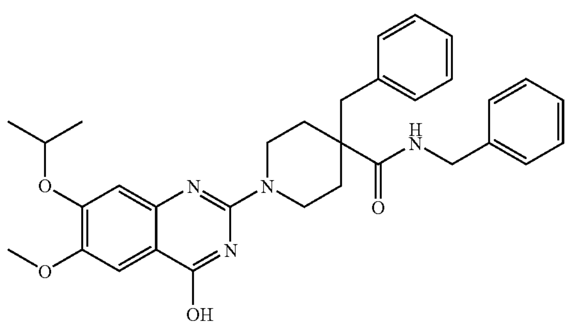 | 4-Benyzl-1-(4-hydroxy-7-isopropoxy-6-methoxy-quinazolin-2-yl)-piperidine-4-carboxylic acid benzylamide | 3-Isopropoxy-4-methoxy-phenylamine (commercially available) and 4-benzyl-piperidine-4-carboxylic acid benzylamide (commercially available) | 541.3 |
| 93 | 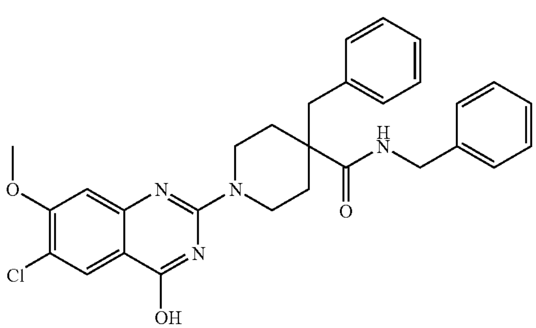 | 4-Benzyl-1-(6-chloro-4-hydroxy-7-methoxy-quinazolin-2-yl)-piperidine-4-carboxylic acid benzylamide | 4-Chloro-3-methoxy-phenylamine (commercially available) and 4-benzyl-piperidine-4-carboxylic acid benzylamide (commercially available) | 517.3 |

TABLE 3-continued

| NO | structure | Systematic Name | starting materials | MW MH+ found |
|---|---|---|---|---|
| 94 | 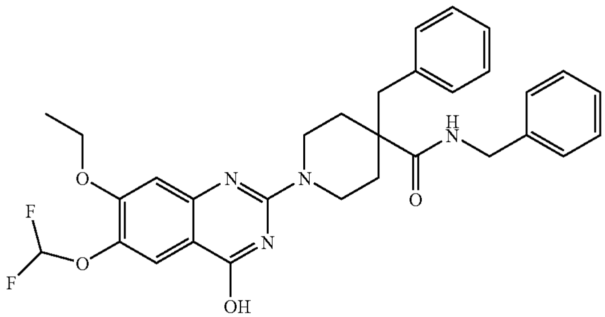 | 4-Benzyl-1-(6-difluoromethoxy-7-ethoxy-4-hydroxy-quinazolin-2-yl)-piperidine-4-carboxylic acid benzylamide | 4-Difluoromethoxy-3-ethoxy-phenylamine (commercially available) and 4-benzyl-piperidine-4-carboxylic acid benzylamide (commercially available) | 563.5 |
| 95 | 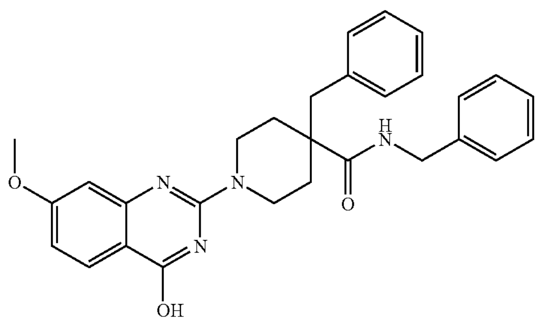 | 4-Benzyl-1-(4-hydroxy-7-methoxy-quinazolin-2-yl)-piperidine-4-carboxylic acid benzylamide | 3-Methoxy-phenylamine (commercially available) and 4-benzyl-piperidine-4-carboxylic acid benzylamide (commercially available) | 483.4 |
| 96 | 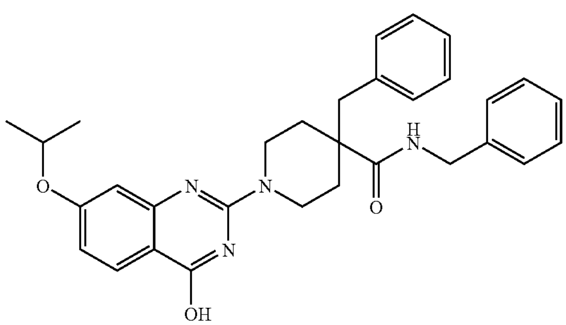 | 4-Benzyl-1-(4-hydroxy-7-isopropoxy-quinazolin-2-yl)-piperidine-4-carboxylic acid benzylamide | 3-Isopropoxy-phenylamine (commercially available) and 4-benzyl-piperidine-4-carboxylic acid benzylamide (commercially available) | 511.4 |
| 97 | 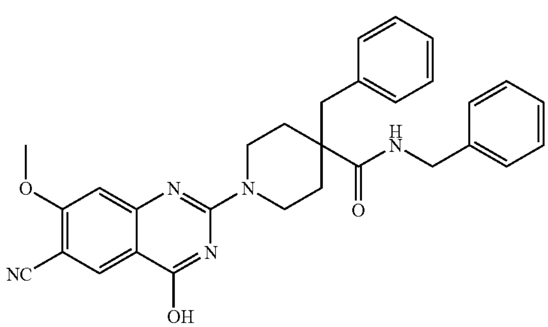 | 4-Benzyl-1-(6-cyano-4-hydroxy-7-methoxy-quinazolin-2-yl)-piperidine-4-carboxylic acid benzylamide | 4-Amino-2-methoxy-benzonitrile (commercially available) and 4-benzyl-piperidine-4-carboxylic acid benzylamide (commercially available) | 508.3 |

TABLE 3-continued

| NO | structure | Systematic Name | starting materials | MW MH+ found |
|---|---|---|---|---|
| 98 | 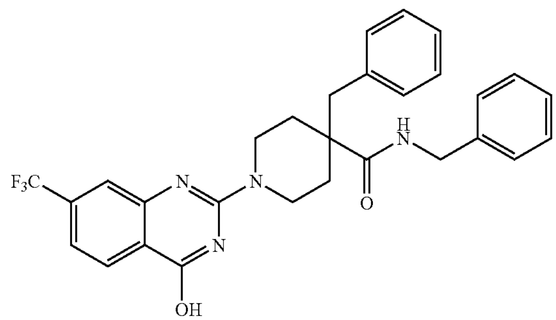 | 4-Benzyl-1-(4-hydroxy-7-trifluoromethyl-quinazolin-2-yl)-piperidine-4-carboxylic acid benzylamide | 3-Trifluoromethyl-phenylamine (commercially available) and 4-benzyl-piperidine-4-carboxylic acid benzylamide (commercially available) | 521.3 |
| 99 | 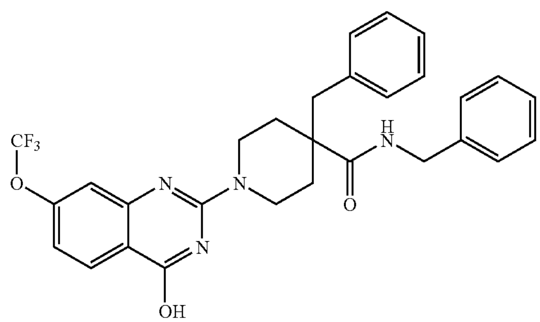 | 4-Benzyl-1-(4-hydroxy-7-trifluoromethoxy-quinazolin-2-yl)-piperidine-4-carboxylic acid benzylamide | 3-Trifluoromethoxy-phenylamine (commercially available) and 4-benzyl-piperidine-4-carboxylic acid benzylamide (commercially available) | 537.4 |
| 100 | 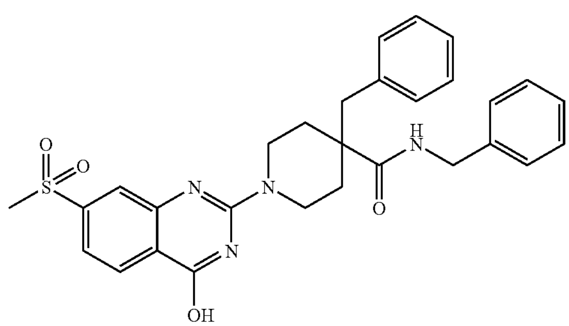 | 4-Benzyl-1-(4-hydroxy-7-methanesulfonyl-quinazolin-2-yl)-piperidine-4-carboxylic acid benzylamide | 3-Methanesulfonyl-phenylamine (commercially available) and 4-benzyl-piperidine-4-carboxylic acid benzylamide (commercially available) | 531.3 |

As mentioned earlier, the compounds of formula I and their pharmaceutically usable addition salts possess valuable pharmacological properties. The compounds of the present invention are antagonists of neurokinin 3 (NK-3) receptors. The compounds were investigated in accordance with the tests given hereinafter.

Experimental Procedure

The compounds were investigated in accordance with the tests given hereinafter
[$^3$H]SR142801 Competition Binding Assay
hNK3 receptor binding experiment were performed using [$^3$H]SR142801 (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM MnCl$_2$, 1 µM phosphoramidon, 0.1% BSA binding buffer at pH 7.4 to a final assay concentration of 5 µg protein/well. For inhibition experiments, membranes were incubated with [$^3$H] SR142801 at a concentration equal to K$_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Canberra Packard S.A., Zürich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). IC$_{50}$ values were derived from the inhibition curve and the affinity constant (K$_i$) values were calculated using the Cheng-Prussoff equation $K_i=IC_{50}/(1+[L]/K_D)$ where [L] is the concentration of radioligand and K$_D$ is its dissociation constant at the receptor, derived from the saturation isotherm. All experiments were performed in duplicate and the mean±standard error (SEM) of the individual $K_i$ values was calculated.

Some results of compounds of the invention with a hNK-3 receptor affinity <0.10 μM were shown in the following table 1.

TABLE 1

| Example | Data $K_i$ [μM] |
|---|---|
| 1 | 0.0909 |
| 2 | 0.0661 |
| 4 | 0.0373 |
| 10 | 0.0183 |
| 14 | 0.0732 |
| 15 | 0.0693 |
| 16 | 0.0347 |
| 17 | 0.0036 |
| 19 | 0.0278 |
| 20 | 0.0463 |
| 23 | 0.0466 |
| 25 | 0.0951 |
| 28 | 0.0524 |
| 33 | 0.0172 |
| 38 | 0.0075 |
| 39 | 0.0036 |
| 40 | 0.0101 |
| 41 | 0.0487 |
| 44 | 0.0054 |
| 46 | 0.0438 |
| 47 | 0.0467 |
| 49 | 0.0206 |
| 51 | 0.0166 |
| 53 | 0.0254 |
| 54 | 0.0048 |
| 55 | 0.0111 |
| 57 | 0.0628 |
| 58 | 0.0038 |
| 59 | 0.0391 |
| 65 | 0.0516 |
| 67 | 0.0479 |
| 68 | 0.0839 |
| 70 | 0.064 |
| 72 | 0.0383 |
| 75 | 0.0478 |
| 76 | 0.0058 |
| 77 | 0.0362 |
| 78 | 0.066 |
| 79 | 0.083 |
| 80 | 0.0076 |
| 83 | 0.0975 |
| 88 | 0.0093 |
| 89 | 0.0115 |
| 90 | 0.0133 |
| 91 | 0.0054 |
| 92 | 0.0215 |
| 93 | 0.0092 |
| 94 | 0.0083 |
| 95 | 0.0051 |
| 96 | 0.0112 |
| 97 | 0.0158 |
| 98 | 0.0061 |
| 99 | 0.0049 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Example A

Tablets of the following composition are manufactured in the usual manner:

| | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

Example B

Capsules of the following composition are manufactured:

| | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelantin capsules.

Example C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The invention claimed is:
1. A compound of formula I

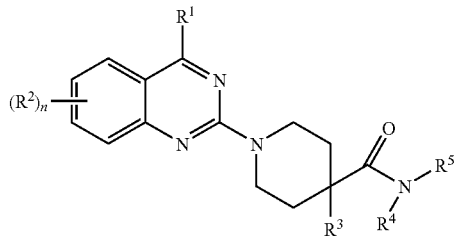

wherein
  $R^1$ is hydroxy or NR'R'';
    R' and R'' are each independently hydrogen, lower alkyl, cycloalkyl, or together with the N-atom to which they are attached form a heteroalkyl ring;
  $R^2$ is hydrogen, lower alkyl, lower alkoxy, halogen, lower alkyl substituted by halogen, lower alkoxy substituted by halogen, cyano or $S(O)_2$-lower alkyl;
  $R^3$ is, —$(CH_2)_m$-aryl optionally substituted by halogen, or —$(CH_2)_m$-cycloalkyl;
  $R^4$ and $R^5$ are each independently
    hydrogen,
    lower alkyl substituted by halogen,
    —$(CR_2)_m$-aryl or —$(CR_2)_m$-heteroaryl, wherein the aryl or heteroaryl is optionally substituted by one or more substituents selected from halogen, lower alkyl, lower alkyl substituted by halogen, cyano, hydroxy, NR'R'' and lower alkoxy substituted by halogen,
    —$(CR_2)_m$-cycloalkyl optionally substituted by hydroxy or by aryl,
    a heteroalkyl ring optionally substituted by =O or —$(CR_2)_m$-aryl, or
    $R^4$ and $R^5$ together with the N-atom to which they are attached form a heterocyclic ring system optionally substituted by lower alkyl, aryl or halogen-substituted aryl,
    each R is independently hydrogen, lower alkyl or lower alkyl substituted by hydroxyl;
  n is 1 or 2; and
  m is 0, 1 or 2;

or a pharmaceutically active salt, a racemic mixture, an enantiomer, an optical isomer or a tautomeric form thereof.

2. The compound of claim 1, wherein $R^3$ is —$(CH_2)_m$-aryl wherein m is 1 and wherein one of $R^4$ or $R^5$ is —$(CH_2)_m$-heteroaryl optionally substituted by methyl wherein m is 0 or 1.

3. The compound of claim 2, selected from the group consisting of
  1-(4-amino-6,7-dimethoxy-quinazolin-2-yl)-4-benzyl-piperidine-4-carboxylic acid (pyridin-3-ylmethyl)-amide;
  4-benzyl-1-(4-hydroxy-6,7-dimethoxy-quinazolin-2-yl)-piperidine-4-carboxylic acid (pyridin-3-ylmethyl)-amide;
  1-(4-amino-6,7-dimethoxy-quinazolin-2-yl)-4-benzyl-piperidine-4-carboxylic acid (furan-2-ylmethyl)-amide; and
  4-benzyl-1-(4-hydroxy-6,7-dimethoxy-quinazolin-2-yl)-piperidine-4-carboxylic acid (1-methyl-1H-pyrazol-4-yl)-amide.

4. The compound of claim 1, wherein $R^3$ is —$(CH_2)_m$-aryl optionally substituted by halogen wherein m is 1 and one of $R^4$ or $R^5$ is —$(CH_2)_m$-phenyl wherein m is 1.

5. The compound of claim 4, selected from the group consisting of
  1-(4-amino-6,7-dimethoxy-quinazolin-2-yl)-4-(4-fluoro-benzyl)-piperidine-4-carboxylic acid benzylamide;
  1-(4-amino-6,7-dimethoxy-quinazolin-2-yl)-4-benzyl-piperidine-4-carboxylic acid benzylamide;
  4-benzyl-1-(4-dimethylamino-6,7-dimethoxy-quinazolin-2-yl)-piperidine-4-carboxylic acid benzylamide;
  4-benzyl-1-(4-cyclopropylamino-6,7-dimethoxy-quinazolin-2-yl)-piperidine-4-carboxylic acid benzylamide;
  4-benzyl-1-(7-chloro-6-fluoro-4-hydroxy-quinazolin-2-yl)-piperidine-4-carboxylic acid benzylamide;
  4-benzyl-1-(4-hydroxy-6,7-dimethoxy-quinazolin-2-yl)-piperidine-4-carboxylic acid benzylamide;
  4-benzyl-1-(4-hydroxy-6,7-dimethoxy-quinazolin-2-yl)-piperidine-4-carboxylic acid benzyl-methyl-amide;
  4-benzyl-1-(4-hydroxy-6-isopropoxy-quinazolin-2-yl)-piperidine-4-carboxylic acid benzylamide;
  4-benzyl-1-(6-fluoro-4-hydroxy-7-methoxy-quinazolin-2-yl)-piperidine-4-carboxylic acid benzylamide;
  4-benzyl-1-(7-difluoromethoxy-4-hydroxy-quinazolin-2-yl)-piperidine-4-carboxylic acid benzylamide; and
  4-benzyl-1-(4-hydroxy-7-methoxy-6-methyl-quinazolin-2-yl)-piperidine-4-carboxylic acid benzylamide.

6. The compound of claim 4, selected from the group consisting of
  4-benzyl-1-(4-hydroxy-6-isopropoxy-7-methoxy-quinazolin-2-yl)-piperidine-4-carboxylic acid benzylamide;
  4-benzyl-1-(4-hydroxy-7-isopropoxy-6-methoxy-quinazolin-2-yl)-piperidine-4-carboxylic acid benzylamide;
  4-benzyl-1-(6-chloro-4-hydroxy-7-methoxy-quinazolin-2-yl)-piperidine-4-carboxylic acid benzylamide;
  4-benzyl-1-(6-difluoromethoxy-7-ethoxy-4-hydroxy-quinazolin-2-yl)-piperidine-4-carboxylic acid benzylamide;
  4-benzyl-1-(4-hydroxy-7-methoxy-quinazolin-2-yl)-piperidine-4-carboxylic acid benzylamide;
  4-benzyl-1-(4-hydroxy-7-isopropoxy-quinazolin-2-yl)-piperidine-4-carboxylic acid benzylamide;
  4-benzyl-1-(6-cyano-4-hydroxy-7-methoxy-quinazolin-2-yl)-piperidine-4-carboxylic acid benzylamide;

4-benzyl-1-(4-hydroxy-7-trifluoromethyl-quinazolin-2-yl)-piperidine-4-carboxylic acid benzylamide; and
4-benzyl-1-(4-hydroxy-7-trifluoromethoxy-quinazolin-2-yl)-piperidine-4-carboxylic acid benzylamide.

7. The compound of claim 1, wherein $R^3$ is —$(CH_2)_m$-aryl wherein m is 1 and one of $R^4$ or $R^5$ is —$(CH_2)_m$-aryl wherein m is 0 and wherein aryl is other than phenyl optionally substituted by hydroxy or halogen.

8. The compound of claim 7, selected from the group consisting of
1-(4-amino-6,7-dimethoxy-quinazolin-2-yl)-4-benzyl-piperidine-4-carboxylic acid indan-2-ylamide;
1-(4-amino-6,7-dimethoxy-quinazolin-2-yl)-4-benzyl-piperidine-4-carboxylic acid (1,2,3,4-tetrahydro-naphthalen-1-yl)-amide;
1-(4-amino-6,7-dimethoxy-quinazolin-2-yl)-4-benzyl-piperidine-4-carboxylic acid (1-hydroxy-indan-2-yl)-amide;
1-(4-amino-6,7-dimethoxy-quinazolin-2-yl)-4-benzyl-piperidine-4-carboxylic acid ((1S,2S)-2-hydroxy-indan-1-yl)-amide;
1-(4-amino-6,7-dimethoxy-quinazolin-2-yl)-4-benzyl-piperidine-4-carboxylic acid (1,2,3,4-tetrahydro-naphthalen-2-yl)-amide;
1-(4-amino-6,7-dimethoxy-quinazolin-2-yl)-4-benzyl-piperidine-4-carboxylic acid indan-1-ylamide;
4-benzyl-1-(4-hydroxy-6,7-dimethoxy-quinazolin-2-yl)-piperidine-4-carboxylic acid indan-2-ylamide;
4-benzyl-1-(4-hydroxy-6,7-dimethoxy-quinazolin-2-yl)-piperidine-4-carboxylic acid indan-2-yl-methyl-amide;
4-benzyl-1-(4-hydroxy-6,7-dimethoxy-quinazolin-2-yl)-piperidine-4-carboxylic acid (1,2,3,4-tetrahydro-naphthalen-2-yl)-amide;
4-benzyl-1-(4-hydroxy-6,7-dimethoxy-quinazolin-2-yl)-piperidine-4-carboxylic acid (5-chloro-1-hydroxy-indan-2-yl)-amide; and
4-benzyl-1-(4-hydroxy-6,7-dimethoxy-quinazolin-2-yl)-piperidine-4-carboxylic acid (1-hydroxy-1,2,3,4-tetrahydro-naphthalen-2-yl)-amide.

9. The compound of claim 1, wherein $R^3$ is —$(CH_2)_m$-aryl wherein m is 1 and one of $R^4$ or $R^5$ is —$(CR_2)_m$-aryl optionally substituted by $OCHF_2$, Cl, or $N(CH_3)_2$ wherein m is 1.

10. The compound of claim 9, selected from the group consisting of
1-(4-amino-6,7-dimethoxy-quinazolin-2-yl)-4-benzyl-piperidine-4-carboxylic acid 4-difluoromethoxy-benzylamide;
1-(4-amino-6,7-dimethoxy-quinazolin-2-yl)-4-benzyl-piperidine-4-carboxylic acid [1-(4-chloro-phenyl)-ethyl]-amide;
1-(4-amino-6,7-dimethoxy-quinazolin-2-yl)-4-benzyl-piperidine-4-carboxylic acid 4-dimethylamino-benzylamide;
1-(4-amino-6,7-dimethoxy-quinazolin-2-yl)-4-benzyl-piperidine-4-carboxylic acid 3,4-dichloro-benzylamide;
1-(4-amino-6,7-dimethoxy-quinazolin-2-yl)-4-benzyl-piperidine-4-carboxylic acid (2-hydroxy-1-phenyl-ethyl)-amide;
1-(4-amino-6,7-dimethoxy-quinazolin-2-yl)-4-benzyl-piperidine-4-carboxylic acid ((R)-1-phenyl-ethyl)-amide; and
1-(4-amino-6,7-dimethoxy-quinazolin-2-yl)-4-benzyl-piperidine-4-carboxylic acid ((R)-1-phenyl-propyl)-amide.

11. The compound of claim 1, wherein $R^3$ is —$(CH_2)_m$-aryl wherein m is 1 and one of $R^4$ or $R^5$ is a heteroalkyl ring optionally substituted by phenyl.

12. The compound of claim 11, which compound is [1-(4-amino-6,7-dimethoxy-quinazolin-2-yl)-4-benzyl-piperidin-4-yl]-(2-phenyl-pyrrolidin-1-yl)-methanone.

13. The compound of claim 1, wherein $R^3$ is —$(CH_2)_m$-aryl wherein m is 1 and one of $R^4$ or $R^5$ is —$(CH_2)_m$-cycloalkyl wherein m is 0 or 1.

14. The compound of claim 13, selected from the group consisting of
4-benzyl-1-(4-hydroxy-6,7-dimethoxy-quinazolin-2-yl)-piperidine-4-carboxylic acid cyclopentylamide and
4-benzyl-1-(4-hydroxy-6,7-dimethoxy-quinazolin-2-yl)-piperidine-4-carboxylic acid cyclobutylmethyl-amide.

15. The compound of claim 1, wherein $R^3$ is —$(CH_2)_m$-cycloalkyl and one of $R^4$ or $R^5$ is —$(CH_2)_m$-aryl wherein m is 0 or 1.

16. The compound of claim 15, selected from the group consisting of
4-cyclopropylmethyl-1-(4-hydroxy-6,7-dimethoxy-quinazolin-2-yl)-piperidine-4-carboxylic acid benzylamide;
4-cyclopropylmethyl-1-(4-hydroxy-6,7-dimethoxy-quinazolin-2-yl)-piperidine-4-carboxylic acid benzyl-methyl-amide;
4-cyclobutylmethyl-1-(4-hydroxy-6,7-dimethoxy-quinazolin-2-yl)-piperidine-4-carboxylic acid benzylamide;
4-cyclobutylmethyl-1-(4-hydroxy-6,7-dimethoxy-quinazolin-2-yl)-piperidine-4-carboxylic acid benzyl-methyl-amide;
4-cyclobutylmethyl-1-(4-hydroxy-6,7-dimethoxy-quinazolin-2-yl)-piperidine-4-carboxylic acid (1,2,3,4-tetrahydro-naphthalen-2-yl)-amide; and
4-cyclobutylmethyl-1-(4-hydroxy-6,7-dimethoxy-quinazolin-2-yl)-piperidine-4-carboxylic acid indan-2-ylamide.

17. The compound of claim 1, wherein $R^3$ is —$(CH_2)_m$-cycloalkyl and one of $R^4$ or $R^5$ is —$(CH_2)_m$-cycloalkyl wherein m is 0.

18. The compound of claim 17, which compound is 4-cyclobutylmethyl-1-(4-hydroxy-6,7-dimethoxy-quinazolin-2-yl)-piperidine-4-carboxylic acid cyclopentylamide.

19. A pharmaceutical composition comprising a therapeutically effective amount of a compound of formula I

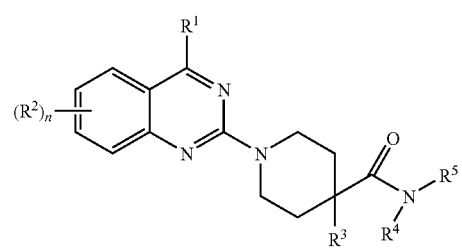

wherein
$R^1$ is hydroxy or NR'R'';
R' and R'' are each independently hydrogen, lower alkyl, cycloalkyl, or together with the N-atom to which they are attached form a heteroalkyl ring;
$R^2$ is hydrogen, lower alkyl, lower alkoxy, halogen, lower alkyl substituted by halogen, lower alkoxy substituted by halogen, cyano or $S(O)_2$-lower alkyl;

$R^3$ is, —$(CH_2)_m$-aryl optionally substituted by halogen, or —$(CH_2)_m$-cycloalkyl;

$R^4$ and $R^5$ are each independently
- hydrogen,
- lower alkyl substituted by halogen,
- —$(CR_2)_m$-aryl or —$(CR_2)_m$-heteroaryl, wherein the aryl or heteroaryl is optionally substituted by one or more substituents selected from halogen, lower alkyl, lower alkyl substituted by halogen, cyano, hydroxy, NR'R" and lower alkoxy substituted by halogen,
- —$(CR_2)_m$-cycloalkyl optionally substituted by hydroxy or by aryl,
- a heteroalkyl ring optionally substituted by =O or —$(CR_2)_m$-aryl, or
- $R^4$ and $R^5$ together with the N-atom to which they are attached form a heterocyclic ring system optionally substituted by lower alkyl, aryl or halogen-substituted aryl, each R is independently hydrogen, lower alkyl or lower alkyl substituted by hydroxyl;

n is 1 or 2; and m is 0, 1 or 2;

or a pharmaceutically active salt, a racemic mixture, an enantiomer, an optical isomer or a tautomeric form thereof and a pharmaceutically acceptable carrier.

* * * * *